United States Patent
McBrien et al.

(10) Patent No.: US 12,349,989 B2
(45) Date of Patent: Jul. 8, 2025

(54) INTERFACING A SURGICAL ROBOTIC ARM AND INSTRUMENT

(71) Applicant: CMR SURGICAL LIMITED, Cambridge, MA (US)

(72) Inventors: Dominic Martin McBrien, Cambridge (GB); James Oliver Grant, Cambridge (GB); Keith Marshall, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 1633 days.

(21) Appl. No.: 16/261,010

(22) Filed: Jan. 29, 2019

(65) Prior Publication Data

US 2019/0231448 A1    Aug. 1, 2019

(30) Foreign Application Priority Data

Jan. 30, 2018 (GB) ...................... 1801539

(51) Int. Cl.
*A61B 34/30* (2016.01)
*A61B 1/00* (2006.01)
(Continued)

(52) U.S. Cl.
CPC .............. *A61B 34/30* (2016.02); *A61B 46/10* (2016.02); *A61B 90/50* (2016.02);
(Continued)

(58) Field of Classification Search
CPC ... A61B 34/30; A61B 2034/305; A61B 34/71; A61B 46/10; A61B 90/50; A61B 1/00149
(Continued)

(56) References Cited

U.S. PATENT DOCUMENTS 8,852,208 B2 * 10/2014 Gomez ..................... H01F 5/04
                                                                  606/1
2010/0204713 A1 * 8/2010 Ruiz Morales .......... B25J 9/041
                                                                  606/130
(Continued)

FOREIGN PATENT DOCUMENTS

CN        106132342 A      11/2016
DE    102016117751 A1       3/2018
(Continued)

OTHER PUBLICATIONS

Shrivastava, Introduction to Plastics Engineering, 2018, Elsevier Science, p. 190 (Year: 2018).*
(Continued)

*Primary Examiner* — Christopher A Flory
(74) *Attorney, Agent, or Firm* — Lando & Anastasi, LLP

(57) ABSTRACT

An interface assembly for detachably interfacing a surgical robot arm to a surgical instrument, the interface assembly comprising: an interface structure comprising: a base portion comprising a first surface for facing the surgical instrument and a second surface for facing the surgical robot arm; and a rear portion attached to a rear edge of the base portion, the rear portion comprising one or more fasteners for fastening the interface structure to a proximal exposed surface of the surgical robot arm; and a locking element moveably mounted on the rear portion, the locking element moveable between a locked position and an unlocked position, wherein when the locking element is in the locked position the locking element biases the one or more fasteners inward and when the locking element is in the unlocked position the locking element does not bias the one or more fasteners inward.

19 Claims, 20 Drawing Sheets

(51) Int. Cl.
　　*A61B 17/00*　　(2006.01)
　　*A61B 34/00*　　(2016.01)
　　*A61B 46/10*　　(2016.01)
　　*A61B 90/00*　　(2016.01)
　　*A61B 90/50*　　(2016.01)
　　*B25J 15/04*　　(2006.01)

(52) U.S. Cl.
　　CPC . *A61B 1/00149* (2013.01); *A61B 2017/00212* (2013.01); *A61B 2017/00477* (2013.01); *A61B 2034/305* (2016.02); *A61B 34/71* (2016.02); *A61B 2090/0808* (2016.02); *B25J 15/04* (2013.01)

(58) Field of Classification Search
　　USPC .............................................................. 606/1
　　See application file for complete search history.

(56) References Cited

U.S. PATENT DOCUMENTS

| | | | | |
|---|---|---|---|---|
| 2015/0173731 | A1* | 6/2015 | Lohmeier | A61B 34/30 |
| | | | | 606/1 |
| 2016/0157941 | A1 | 6/2016 | Anvari et al. | |
| 2016/0242861 | A1 | 8/2016 | Flatt et al. | |
| 2017/0079727 | A1 | 3/2017 | Crawford et al. | |
| 2018/0318020 | A1* | 11/2018 | Thompson | A61B 34/70 |

FOREIGN PATENT DOCUMENTS

| | | | | |
|---|---|---|---|---|
| GB | 2538230 | A * | 11/2016 | ............ A61B 34/30 |
| GB | 2552540 | A | 1/2018 | |
| GB | 2552855 | A | 2/2018 | |
| GB | 2553879 | A | 3/2018 | |
| JP | 2009213653 | A | 9/2009 | |
| JP | 2018500070 | A | 1/2018 | |
| WO | 2016209891 | A1 | 12/2016 | |
| WO | 2018051093 | A1 | 3/2018 | |

OTHER PUBLICATIONS

Japanese Notification of Reasons for Refusal from corresponding Japanese Application No. 2020-541573 dated Mar. 15, 2022.
United Kingdom Search Report from corresponding United Kingdom Application No. GB1801539.6 dated Jun. 28, 2018.
International Search Report from corresponding PCT/GB2019/050237 dated May 10, 2019.
Chinese First Office Action from corresponding Chinese Application No. 201980021851.5 dated Aug. 17, 2023.
Australian Examination Report No. 1 from corresponding Australian Application No. 2022204385 dated Sep. 8, 2023.

* cited by examiner

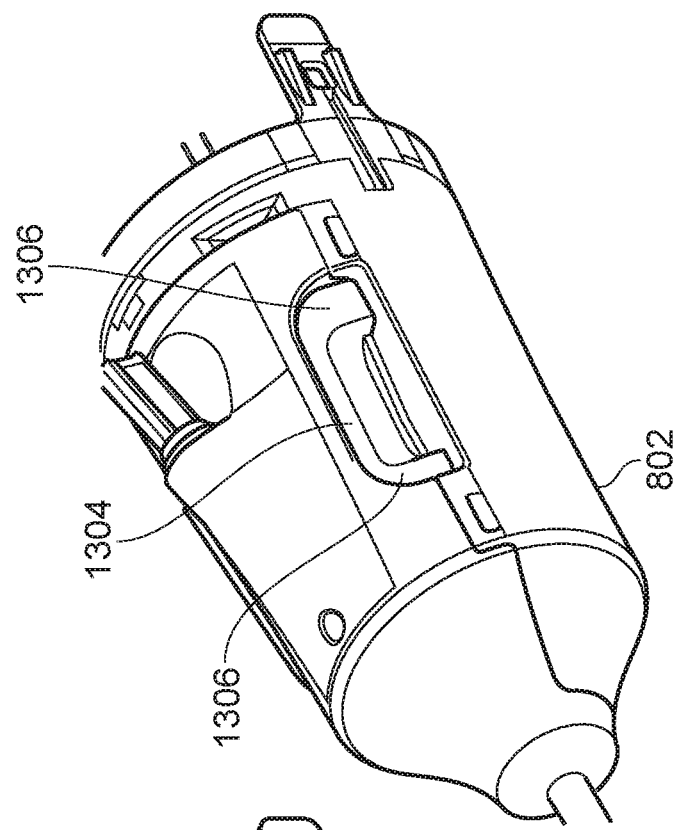
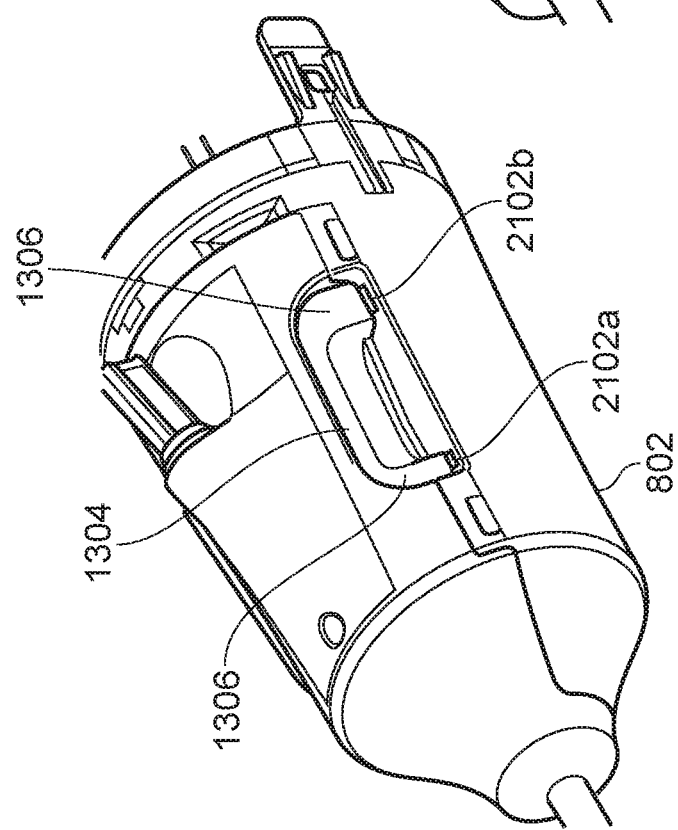
FIG. 21A
FIG. 21B

INTERFACING A SURGICAL ROBOTIC ARM AND INSTRUMENT

CROSS-REFERENCE TO RELATED APPLICATION

This application claims the benefit under 35 U.S.C. § 119 of United Kingdom Patent Application No. 1801539.6 filed on Jan. 30, 2018 which is hereby incorporated herein by reference in its entirety for all purposes.

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

FIG. 2 illustrates a typical surgical instrument 200 for performing robotic laparoscopic surgery. The surgical instrument comprises a base 201 by means of which the surgical instrument connects to the robot arm. A shaft 202 extends between base 201 and articulation 203. Articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

A surgeon utilises many instruments during the course of a typical laparoscopy operation. For this reason, it is desirable for the instruments to be detachable from and attachable to the end of the robot arm with an ease and speed which enables instruments to be exchanged mid-operation. It is therefore desirable to minimise the time taken and maximise the ease with which one instrument is detached from a robot arm and a different instrument is attached.

The operating theatre is a sterile environment. The surgical robotic system must be sterile to the extent it is exposed to the patient. Surgical instruments are sterilised prior to use in an operation, however the robot arm is not sterilised prior to use. Instead, a sterile drape is placed over the whole of the surgical robot prior to the operation. In this way, the patient is not exposed to the non-sterile surgical robot arm. When exchanging instruments mid-operation, it is desirable for the sterile barrier to be maintained.

SUMMARY OF THE INVENTION

According to a first aspect of the invention, there is provided an interface assembly for detachably interfacing a surgical robot arm to a surgical instrument, the interface assembly comprising: an interface structure comprising: a base portion comprising a first surface for facing the surgical instrument and a second surface for facing the surgical robot arm; and a rear portion attached to a rear edge of the base portion, the rear portion comprising one or more fasteners for engaging a proximal exposed surface of the surgical robot arm so as to fasten the interface structure to the surgical robot arm; and a locking element moveably mounted on the rear portion, the locking element moveable between a locked position and an unlocked position, wherein when the locking element is in the locked position the locking element biases the one or more fasteners towards an engaged position and when the locking element is in the unlocked position the locking element does not bias the one or more fasteners towards the engaged position.

The locking element may be slideable between the locked position and the unlocked position.

The locking element may have a substantially cylindrical inner surface.

The rear portion may comprises a collar with a substantially cylindrical inner surface and the locking element may be moveable along the collar.

The cylindrical collar may be configured to have an interference fit around a shoulder of the surgical robot arm when the interface assembly is brought into engagement with the surgical robot arm.

An outer surface of one or more of the fasteners may comprise one or more sloped protrusions, the depth of the sloped protrusions increasing in a direction in which the locking element moves from the unlocked position to the locked position.

The locking element may comprise one or more juts and each jut is configured to engage a corresponding detent in the rear portion when the locking element is in the locked position.

The one or more juts and the corresponding detents may be configured to generate feedback when the one or more juts come into engagement with the corresponding detents.

A front surface of the locking element may comprise one or more tabs configured to be received in an opening in the surgical instrument when the surgical instrument is brought into engagement with the interface assembly so as to restrict movement of the locking element from the locked position when the surgical instrument is engaged with the interface assembly.

An inner surface of the locking element may comprise one or more retention protrusions that engage a rear surface of the rear portion when the locking element is in the unlocked position so as to retain the locking element on the interface structure when the locking element is in the unlocked position.

An inner surface of the locking element may comprise one or more ribs that engage corresponding channels in an outer surface of the rear portion so as to prevent the locking element from rotating with respect to the interface structure.

The interface structure may further comprise an envelope portion which connects opposing edges of the base portion so as to, when engaged on the surgical robot arm, retain the interface structure to the surgical robot arm.

The envelope portion is shaped so as to, when the interface structure is engaged on the surgical robot arm, circumscribe an exterior surface of the surgical robot arm.

The base portion and the envelope portion may be integrally formed.

The locking element may terminate in a drape.

The drape and the locking element may be integrally formed.

The base portion may comprise an oval pin that is received in a circular recess in the surgical instrument when the surgical instrument is in engagement with the interface assembly.

The oval pin may be longest in a direction transverse to a longitudinal axis of the interface structure.

The base portion may comprise a round pin that is received in a slot-shaped recess in the surgical instrument when the surgical instrument is in engagement with the interface assembly.

The interface structure may comprise on or more tabs that bear against features of the instrument in a direction parallel to a longitudinal axis of the interface assembly when the instrument is in engagement with the interface assembly so as to axially align the instrument with the interface assembly.

An inner surface of the interface structure may comprise a pin that engages a corresponding slot-shaped recess in an outer surface of the surgical robot arm when the interface assembly is engaged with the surgical robot so as to retain movement of the interface structure in a direction perpendicular to a longitudinal axis of the interface structure.

The base portion may comprise a rim having the first surface and the second surface, the rim surrounding a hollow interior.

The rim may have an opening which is configured to receive a portion of the instrument, the opening being valley-shaped with valley walls.

An outer surface of one or more of the valley walls may comprise one or more ribs which engage the portion of the instrument when the instrument is in engagement with the interface assembly.

The rear portion may comprise a rear wing portion attached to a rear edge of the rim of the base portion, the rear wing portion configured to cover a proximal exposed surface of the surgical robot arm.

The rear wing portion may be angled relative to the base portion away from a distal end of the surgical robot arm.

The interface structure may further comprise a front wing portion attached to a front edge of the rim of the base portion, the front wing portion configured to cover a distal exposed surface of the surgical robot arm.

The base portion may comprise one or more instrument engagement markings that are visible when a surgical instrument is not fully attached to the interface assembly and that are not visible when a surgical instrument is fully attached to the interface assembly.

The one or more instrument engagement markings may be configured to be concealed by a moveable portion of the surgical instrument when the surgical instrument is fully attached to the interface assembly.

When the interface assembly is attached to the surgical robot arm, the base portion may be parallel to an axial direction of the surgical robot arm.

The locking element may be rotatable between the locked position and the unlocked position According to a first aspect of the invention, there is provided a surgical robot arm for use in robotic surgery, the surgical robot arm comprising: a base; and a series of articulations connecting the base to an interfacing portion at the distal end of the surgical robot arm, the series of articulations enabling the interfacing portion to be articulated relative to the base; and the interfacing portion configured to interface a surgical instrument by retaining the interface assembly of the first aspect.

BRIEF DESCRIPTION OF THE FIGURES

The present invention will now be described by way of example with reference to the accompanying drawings. In the drawings:

FIG. 21A illustrates an instrument partially attached to the interface structure of FIG. 8 such that the instrument attachment markings are visible;
and
FIG. 21B illustrates an instrument fully attached to the interface structure of FIG. 8 such that instrument attachment markings are not visible;

DETAILED DESCRIPTION

Figure 3:
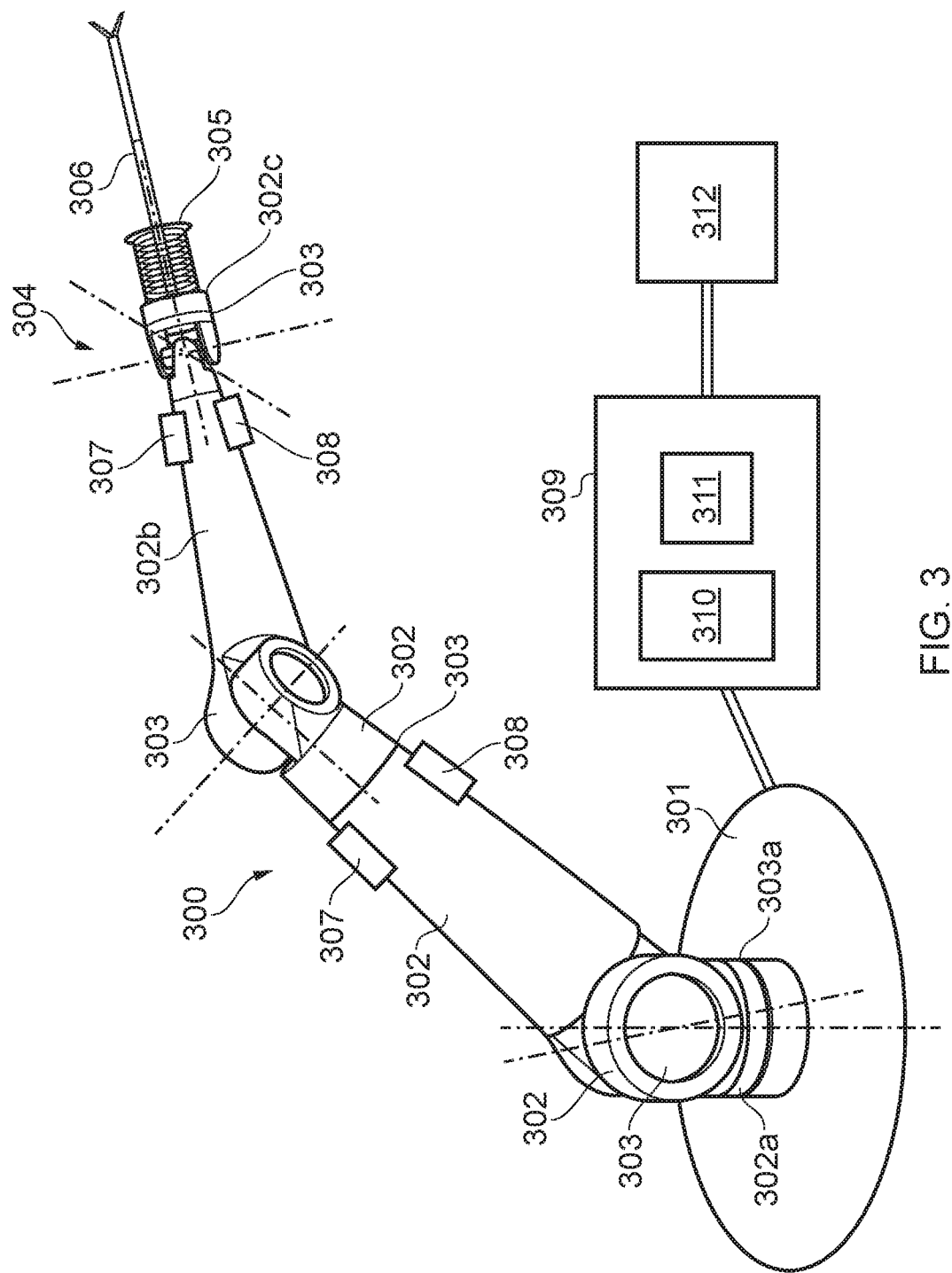
FIG. 3 illustrates a surgical robot.

FIG. 3 illustrates a surgical robot having an arm 300 which extends from a base 301. The arm comprises a number of rigid limbs 302. The limbs are coupled by revolute joints 303. The most proximal limb 302a is coupled to the base by joint 303a. It and the other limbs are coupled in series by further ones of the joints 303. Suitably, a wrist 304 is made up of four individual revolute joints. The wrist 304 couples one limb (302b) to the most distal limb (302c) of the arm. The most distal limb 302c carries an attachment 305 for a surgical instrument 306. Each joint 303 of the arm has one or more motors 307 which can be operated to cause rotational motion at the respective joint, and one or more position and/or torque sensors 308 which provide information regarding the current configuration and/or load at that joint. Suitably, the motors are arranged proximally of the joints whose motion they drive, so as to improve weight distribution. For clarity, only some of the motors and sensors are shown in FIG. 3. The arm may be generally as described in our co-pending patent application PCT/GB2014/053523.

Figure 1:
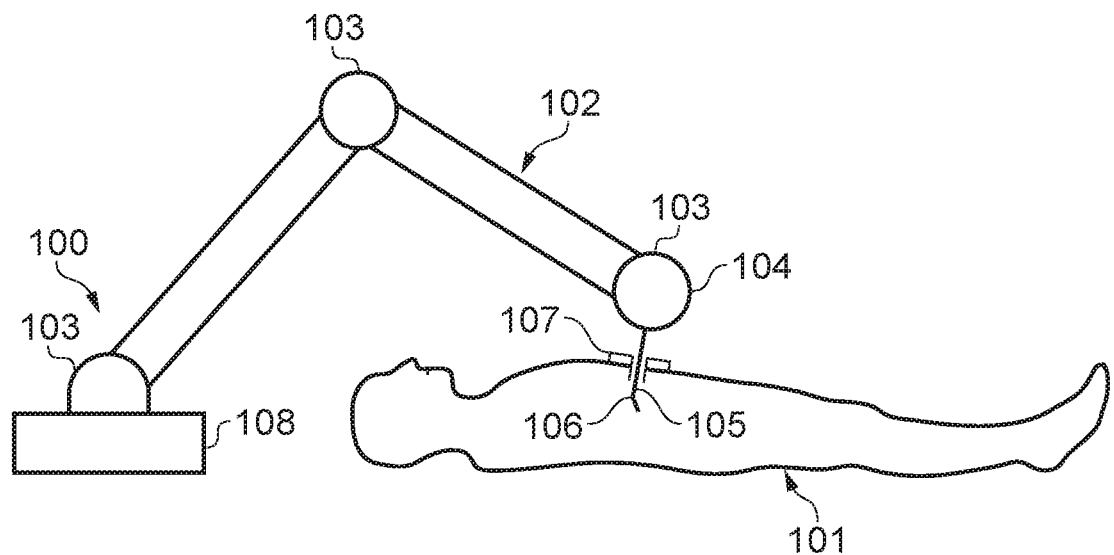
FIG. 1 illustrates a surgical robot performing a surgical procedure.
Figure 2:
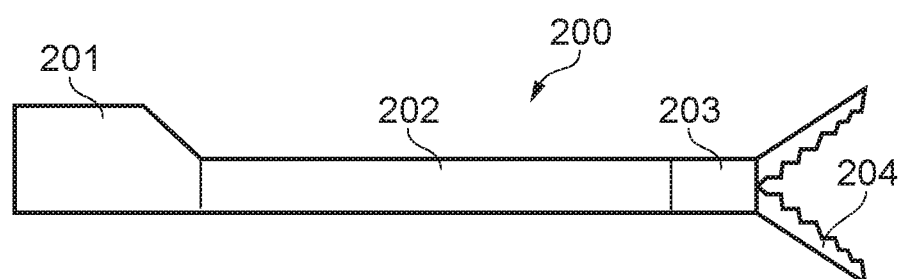
FIG. 2 illustrates a known surgical instrument.

The arm terminates in an attachment 305 for interfacing with the instrument 306. Suitably, the instrument 306 takes the form described with respect to FIG. 2. The instrument has a diameter less than 8 mm. Suitably, the instrument has a 5 mm diameter. The instrument may have a diameter which is less than 5 mm. The instrument diameter may be the diameter of the shaft. The instrument diameter may be the diameter of the profile of the articulation. Suitably, the diameter of the profile of the articulation matches or is narrower than the diameter of the shaft. The attachment 305 comprises a drive assembly for driving articulation of the instrument. Movable interface elements of the drive assembly interface mechanically engage corresponding movable interface elements of the instrument interface in order to transfer drive from the robot arm to the instrument. One instrument is exchanged for another several times during a typical operation. Thus, the instrument is attachable and detachable from the robot arm during the operation. Features of the drive assembly interface and the instrument interface aid their alignment when brought into engagement with each other, so as to reduce the accuracy with which they need to be aligned by the user.

The instrument 306 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation comprises several joints which permit the end effector to move relative to the shaft of the instrument. The joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed with the robot arm. The controllers are connected via a communication bus to control unit 309. A control unit 309 comprises a processor 310 and a memory 311. Memory 311 stores in a non-transient way software that is executable by the processor to control the operation of the motors 307 to cause the arm 300 to operate in the manner described herein. In particular, the software can control the processor 310 to cause the motors (for example via distributed controllers) to drive in dependence on inputs from the sensors 308 and from a surgeon command interface 312. The control unit 309 is coupled to the motors 307 for driving them in accordance with outputs generated by execution of the software. The control unit 309 is coupled to the sensors 308 for receiving sensed input from the sensors, and to the command interface 312 for receiving input from it. The respective couplings may, for example, each be electrical or optical cables, or may be provided by a wireless connection. The command interface 312 comprises one or more input devices whereby a user can request motion of the end effector in a desired way. The input devices could, for example, be manually operable mechanical input devices such as control handles or joysticks, or contactless input devices such as optical gesture sensors. The software stored in memory 311 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, a surgeon at the command interface 312 can control the instrument 306 to move in such a way as to perform a desired surgical procedure. The control unit 309 and/or the command interface 312 may be remote from the arm 300.

Figure 4:
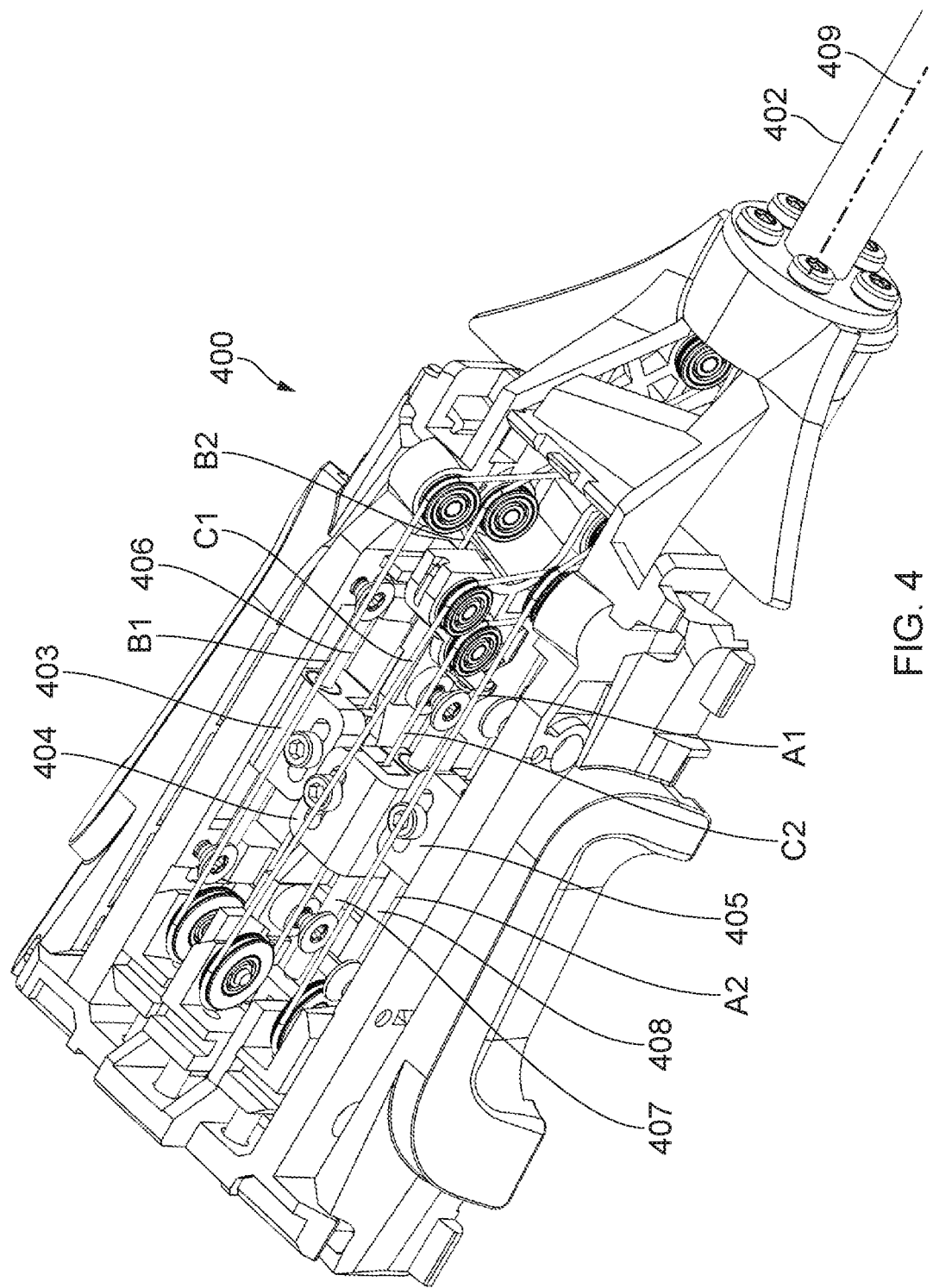
FIG. 4 illustrates a top view of an instrument interface.
Figure 5:
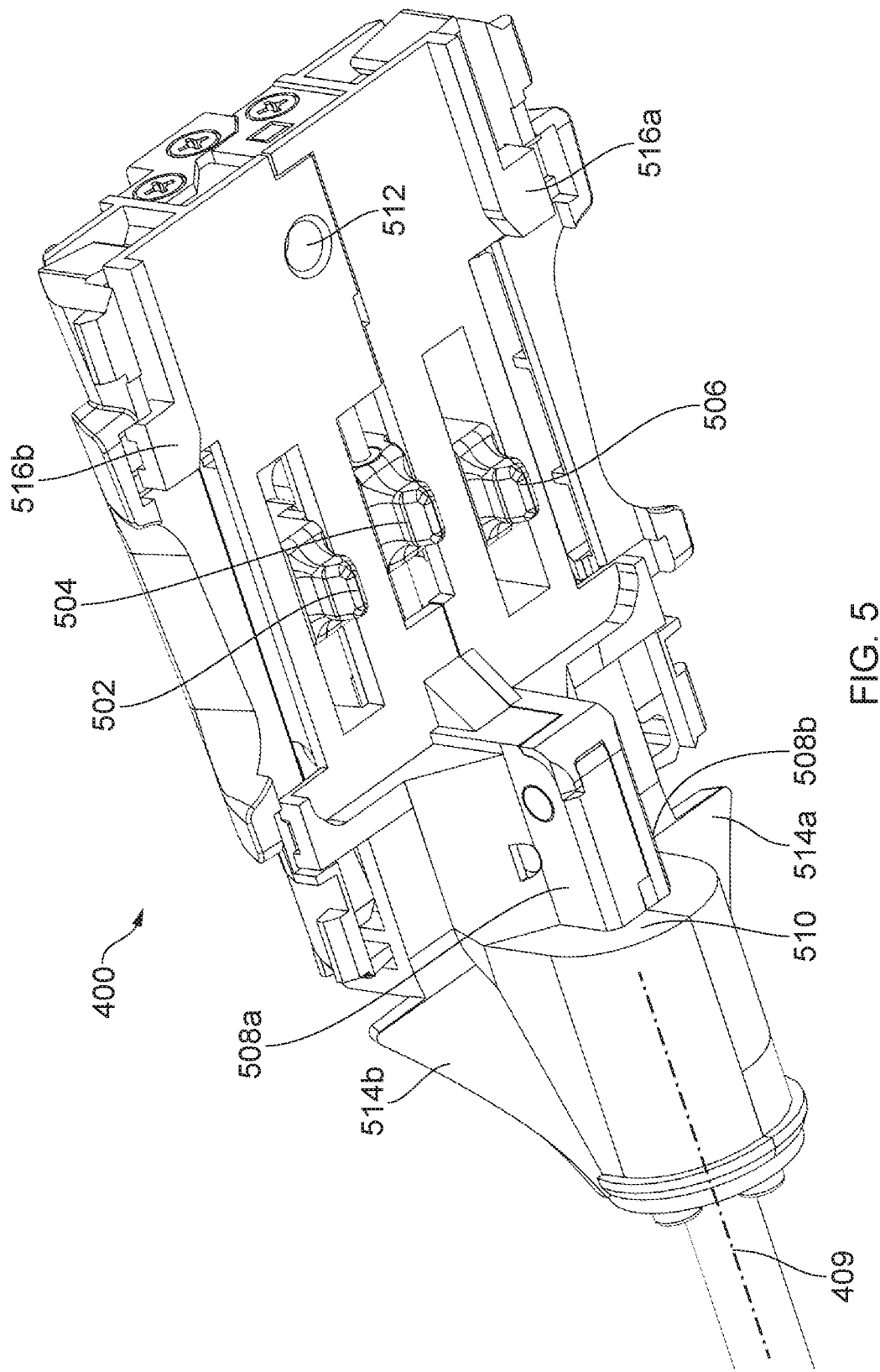
FIG. 5 illustrates a bottom view of the instrument interface of FIG. 4.
Figure 6:
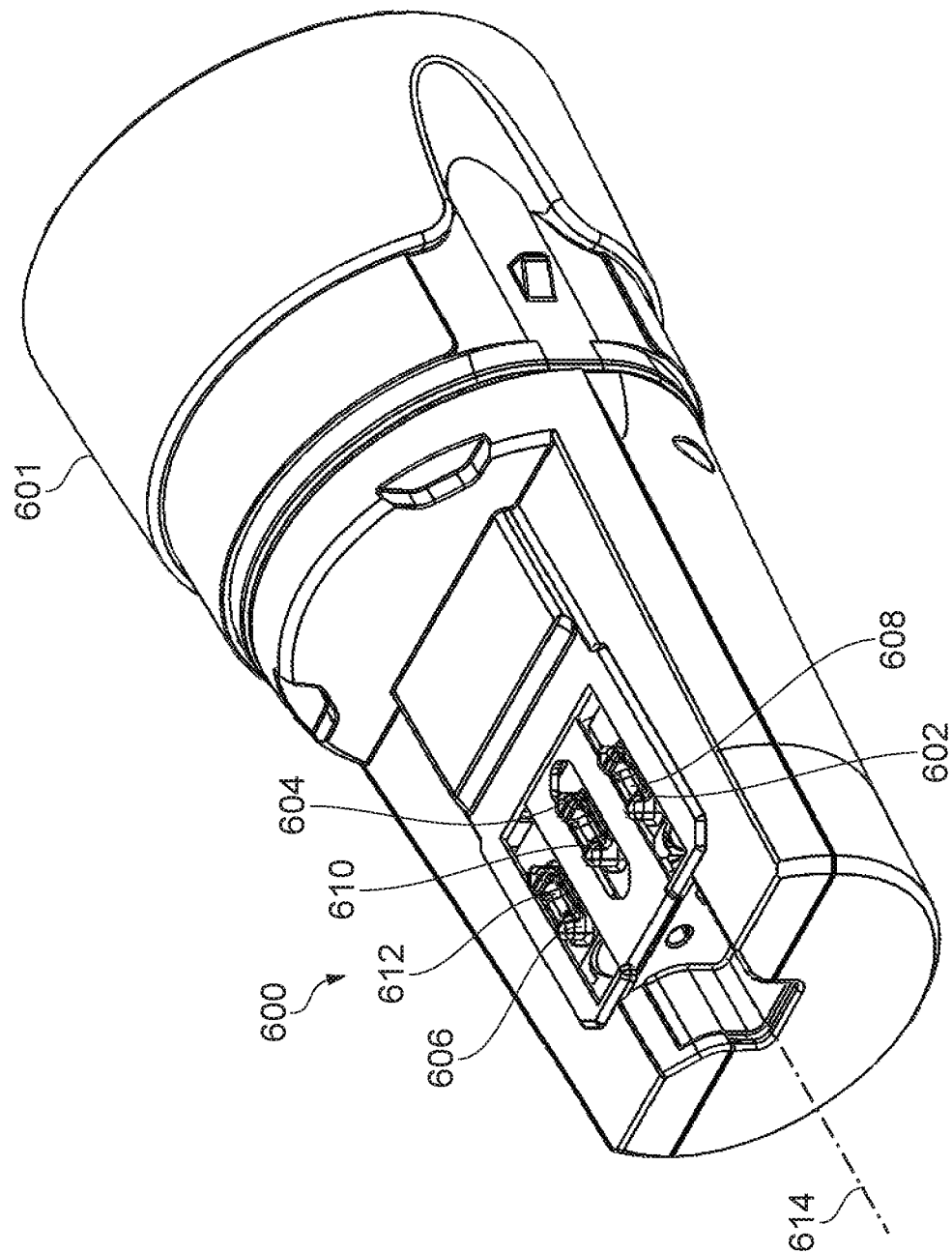
FIG. 6 illustrates a drive assembly interface of a robot arm with attached interface structure.

FIGS. 4 to 6 illustrate an exemplary mechanical interconnection of the drive assembly interface and the instrument interface in order to transfer drive from the robot arm to the instrument. The shaft 402 of the instrument terminates in the instrument interface 400. The instrument interface 400 comprises a plurality of instrument interface elements 403, 404, 405. Pairs of driving elements (A1, A2), (B1, B2), (C1, C2) extend into the instrument interface 400 from the end of the shaft 402. Each pair of driving elements terminates in one of the instrument interface elements. In the example shown in FIG. 4: driving element pair A1, A2 terminates in instrument interface element 405; driving element pair B1, B2 terminates in instrument interface element 403; and driving element pair C1, C2 terminates in instrument interface element 404.

FIGS. 4 and 5 illustrate three instrument interface elements and three driving element pairs. In other examples, there may be greater than or fewer than three instrument interface elements. There may be greater than or fewer than three driving element pairs. In FIGS. 4 and 5 there is a one-to-one relationship between instrument interface elements and driving element pairs. In other examples, there may be any other coupling relationship between the instrument interface elements and driving element pairs. For example, a single instrument interface element may drive more than one pair of driving elements. In another example, more than one instrument interface element may drive a single pair of driving elements.

The instrument interface elements are displaceable within the instrument interface. In the example shown, the instrument interface elements are slideable along rails. Instrument interface element 403 is slideable along rail 406, instrument interface element 404 is slideable along rail 407, and instrument interface element 405 is slideable along a rail 408. Each instrument interface element is displaceable along a direction parallel to the direction of elongation of the pair of driving elements which that instrument interface element holds captive. Each instrument interface element is displaceable in a direction parallel to the longitudinal axis 409 of the instrument shaft 402. When the instrument interface element moves along its rail, it causes a corresponding movement to the driving element pair secured to it. Thus, moving an instrument interface element drives motion of a driving element pair and hence motion of a joint of the instrument.

In the example of FIGS. 4 and 5, each instrument interface element comprises a fin 502, 504, 506 (FIG. 5) which is the portion of the instrument interface element which engages the drive assembly interface element.

In another example, each drive assembly interface element comprises a fin, and each instrument interface element comprises a socket for receiving the fin of the corresponding drive assembly interface element.

FIG. 6 illustrates an exemplary drive assembly interface 600 at the end of a robot arm 601. Drive assembly interface 600 mates with instrument interface 400. Drive assembly interface 600 comprises structure for receiving the instrument interface elements of the instrument interface of FIGS. 4-5. Specifically, drive assembly interface elements 602, 604, 606 receive instrument interface elements 403, 404, 405. In the example shown, each drive assembly interface element comprises a socket for receiving the fin 502, 504, 506 of the corresponding instrument interface element. Socket 608 of drive assembly interface element 602 receives fin 502 of instrument interface element 403. Socket 610 of drive assembly interface element 604 receives fin 504 of instrument interface element 404. Socket 612 of drive assembly interface element 606 receives fin 506 of instrument interface element 405.

FIG. 6 illustrates three drive assembly interface elements. In other examples, there may be greater than or fewer than three drive assembly interface elements. In FIGS. 4-6 there is a one-to-one relationship between instrument interface elements and drive assembly interface elements. In other examples, there may be any other coupling relationship between the instrument interface elements and drive assembly interface elements. For example, a single drive assembly interface element may drive more than one instrument interface element. In another example, more than one drive assembly interface element may drive a single instrument interface element.

Each drive assembly interface element is displaceable within the drive assembly. This displacement is driven. For example, the displacement may be driven by a motor and lead screw arrangement. In the example shown, the drive assembly interface elements are slideable along rails. Each drive assembly interface element is displaceable along a direction parallel to the longitudinal axis 614 of the terminal link of the robot arm. When the drive assembly interface element moves along its rail, it causes a corresponding movement to the instrument interface element that it holds captive. Thus, driving motion of a drive assembly interface element drives motion of an instrument interface element which drives articulation of the end effector of the instrument.

Figure 7:
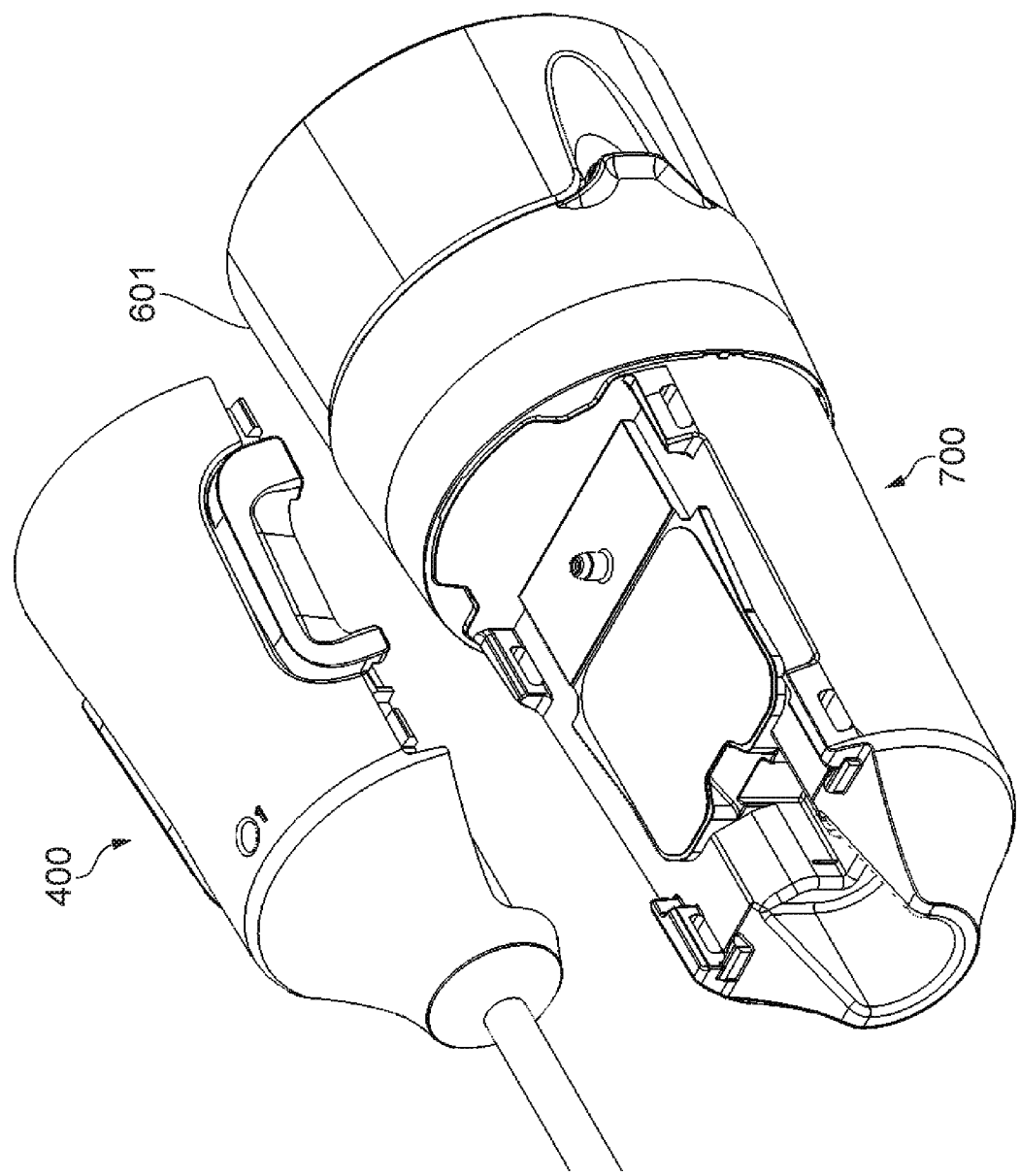
FIG. 7 illustrates an instrument being positioned into engagement with a robot arm.

FIG. 7 illustrates the instrument being placed into engagement with the robot arm. When instrument interface element 403 and drive assembly interface element 602 are engaged, instrument interface element 404 and drive assembly interface element 604 are engaged, and instrument interface element 405 and drive assembly interface element 606 are engaged, the instrument interface elements and the drive assembly interface elements are all displaceable in the same direction. This direction is parallel to both the longitudinal axis 614 of the terminal link of the robot arm and the longitudinal axis 409 of the instrument shaft.

During an operation, the surgical robot is shrouded in a sterile drape to provide a sterile barrier between the non-sterile surgical robot and the sterile operating environment. The surgical instrument is sterilised before being attached to the surgical robot. The sterile drape is typically constructed of a plastic sheet, for example made of polyester, polypropylene, polyethylene or polytetrafluoroethylene (PTFE). Suitably, the drape is flexible and/or deformable.

The sterile drape does not pass directly between the drive assembly interface 600 and the instrument interface 400. An interface assembly 700 is attached to the drape for interfacing between the drive assembly interface 600 and the instrument interface 400.

Figure 8:
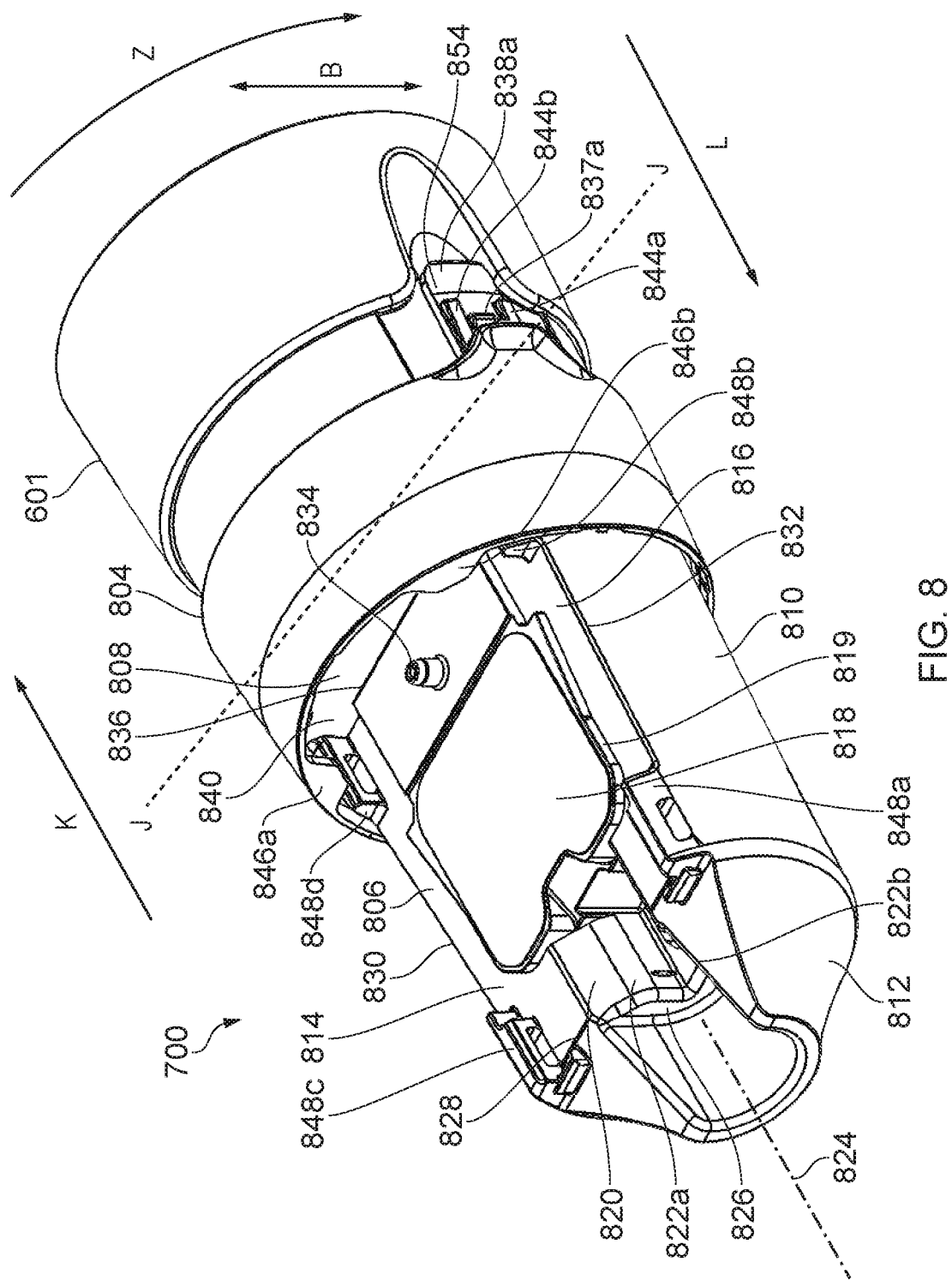
FIG. 8 illustrates an interface assembly with a locking element when the locking element is in the unlocked position.
Figure 9:
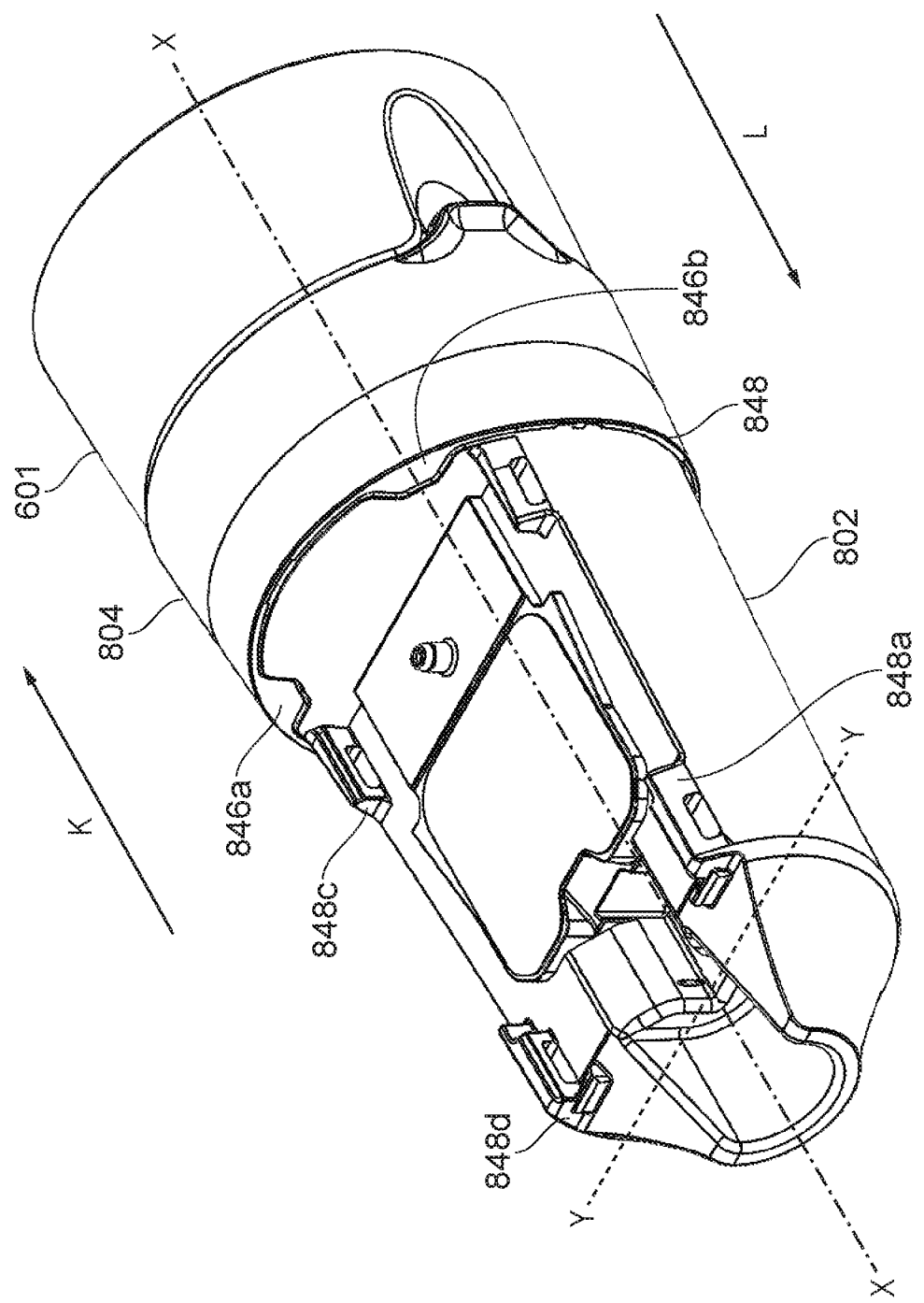
FIG. 9 illustrates the interface assembly of FIG. 8 when the locking element is in the locked position.

FIGS. 8 and 9 show an exemplary interface assembly 700 attached to a robot arm 601. The interface assembly 700 comprises an interface structure 802 for interfacing between the drive assembly interface 600 and the instrument interface 400, and a moveable locking element 804 for locking the interface structure 802 onto the robot arm. Suitably the drape is attached to the locking element 804. However, in other examples the drape may be attached to the interface structure 802. The interface structure 802 or the locking element 804 may be integrally formed with the drape. Alternatively, the interface structure 802 or the locking element 804 may be formed separately from the drape and subsequently attached to the drape. Either way, the interface assembly 700 is sterile. One side of the interface structure 802 directly contacts the drive assembly interface. Another side of the interface structure 802 directly contacts the instrument interface. Thus, the interface structure 802 prevents the non-sterile drive assembly interface from directly touching the sterile instrument interface and hence maintains the sterile barrier between the two components.

Suitably, the interface structure 802 is a single moulded part. The exemplary interface structure 802 of FIGS. 8-9 comprises a base portion 806 and rear portion 808. The interface structure may also comprise an envelope portion 810 and/or a front wing portion 812. Suitably, when the interface structure 802 is attached to the surgical robot arm, the base portion 806 lies parallel to the axial direction of the terminal link of the robot arm. The base portion 806 comprises a first surface 814 which faces the surgical instrument when the instrument is attached to the robot arm. Specifically, the first surface 814 faces the instrument interface 400. The base portion 806 comprises a second surface (not visible on FIGS. 8-9) which opposes the first surface 814. The second surface faces the robot arm when the instrument is attached to the robot arm. Specifically, the second surface faces the drive assembly interface 600. The first surface 814 may be flat. The second surface may be flat.

The base portion 806 of the interface structure 802 comprises a rim 816 surrounding a hollow interior 818. When the interface structure 802 is attached to the robot arm, the rim 816 is encompassed within a boundary formed by the external surface of the surgical robot arm in the longitudinal direction of the surgical robot arm. The rim 816 has an opening 820 which receives the portion of the chassis of the instrument interface 400 into which the end of the shaft of the surgical instrument terminates. The opening 820 is valley-shaped, with valley walls 822a and 822b. The instrument interface 400 has contact faces 508a and 508b, which have a complementary shape to the valley walls 822a, 822b such that contact faces 508a, 508b engage valley walls 822a, 822b when the instrument interface is engaged in the interface structure. Suitably, the contact faces 508a, 508b have a light interference fit to the valley walls 822a, 822b. The engagement of the contact faces and valley walls acts to prevent motion of the instrument parallel to the base portion 806 and transverse to the longitudinal axis 824 of the interface structure 802. The engagement of the contact faces and valley walls acts to prevent rotational motion of the instrument about the longitudinal axis 824 of the interface structure 802. The instrument interface 400 suitably has a contact face 510 which abuts a contact face 826 of the opening 820 when the instrument interface is engaged in the interface structure. The contact face 826 is transverse to the longitudinal axis 824. The contact face 826 is parallel to the front edge 828 of the base portion. The front edge 828 joins the two longer outer edges 830 and 832 of the base portion.

The base portion 806 may comprise a pin 834. Pin 834 may be located on the longitudinal axis 824 of the interface structure 802. Instrument interface 400 may comprise a recess 512 into which the pin 834 of the interface structure 802 engages. Recess 512 may be located on the longitudinal axis 409 of the instrument interface 400. The pin 834 fits snugly into the recess 512.

The engagement of the pin 834 in the recess 512, and the bearing of the contact face 510 on the contact face 826 cause the instrument to be aligned axially with the interface structure. They also act to restrain movement of the instrument relative to the interface structure in the axial direction.

The hollow interior 818 receives the instrument interface elements which engage with the drive assembly interface elements. Suitably, a flexible material covers the hollow interior 818. In some cases, the flexible material may be bonded to the rim 819 of the hollow interior 818. In other cases the flexible material may be removably attached to the instrument structure so as to cover the hollow interior 818. In either case, the flexible material provides a sterile barrier between the instrument interface elements and the drive assembly interface elements. The flexible material may be a resilient, low modulus material with good resistance to puncture and tearing. It some cases the flexible material may be a styrenic block copolymer, such as those sold under the name Kraton®.

Alternatively, the base portion 806 may support movable covers (not shown) for the drive assembly interface elements, so that the instrument interface elements do not directly contact the drive assembly interface elements, but instead engage the drive assembly interface elements via the movable covers. For example, the base portion 806 may support one moveable cover for each instrument interface element that is configured to receive that instrument interface element, and to be received by the corresponding drive assembly interface element. Each moveably cover is a snug fit into its respective drive assembly interface element, and each movable cover fits its respective interface element. Thus the drive is effectively transferred though the interface structure from the drive assembly interface to the instrument interface. The rim 816 may surround a hollow interior 818 which houses all the moveable covers. Alternatively, the rim 816 may surround three hollow interiors, each of which houses a single one of the moveable covers.

The rear portion 808 is attached to the rear edge 836 of the rim 816 of the base portion. Both the rear edge 836 and the front edge 828 join the two longer outer edges 830 and 832 of the base portion. When the interface structure 802 is attached to the robot arm, the front edge 828 is positioned closer to the free distal end of the robot arm than the rear edge 836. The rear portion 808 comprises one or more first fasteners 838a, 838b for fastening the rear portion 808 to a proximal exposed surface of the robot arm. In the example shown in FIGS. 8-9, there are two first fasteners 838a, 838b which are each in the form of a clip with an aperture 837a, 837b which is configured to clip onto a lug 839a, 839b of a slip collar of the robot arm. Any suitable fastener may be used for the first fastener. The rear portion 808 may be integrally moulded with the base portion 806.

Figure 15:
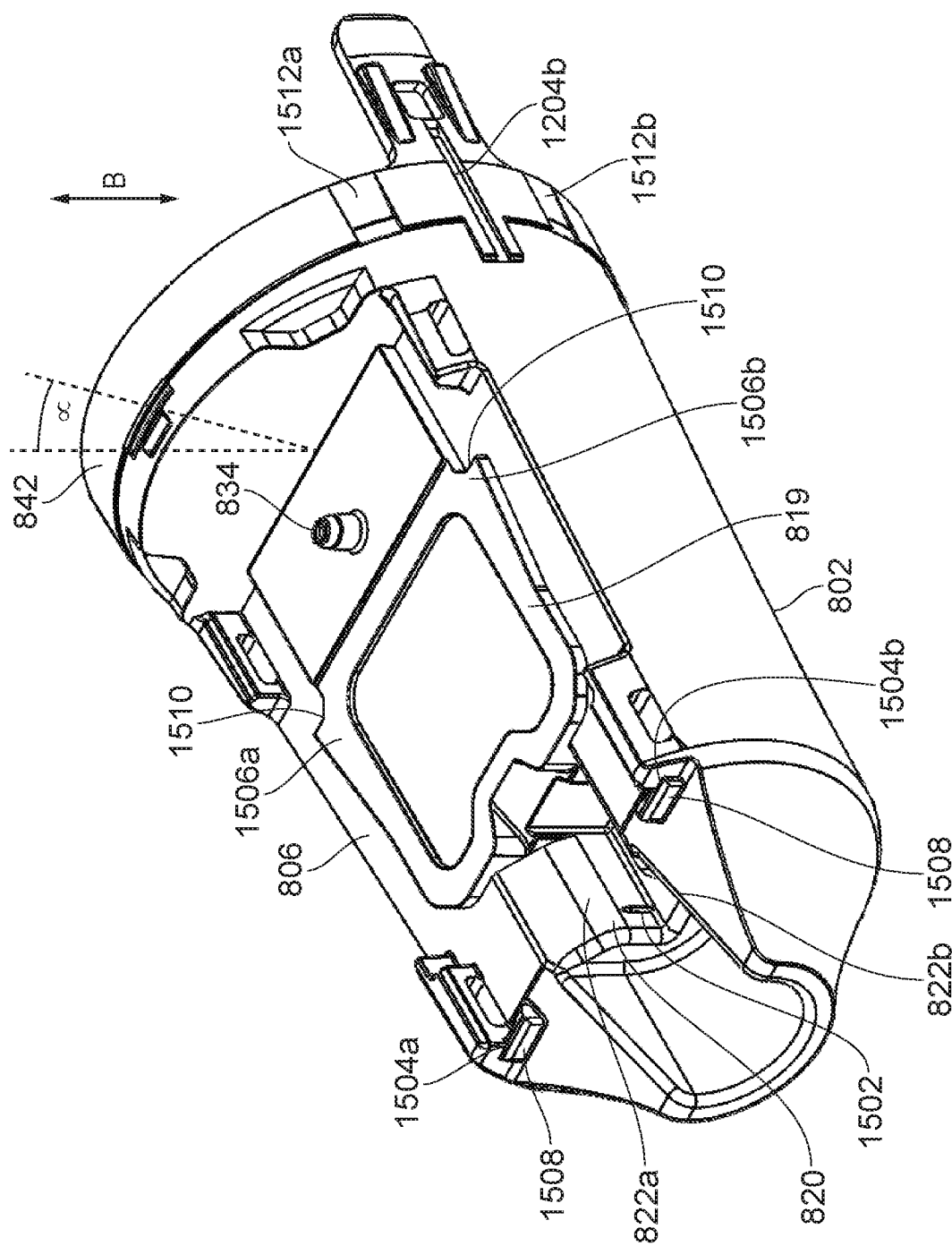
FIG. 15 illustrates an interface structure of FIG. 8 in isolation.

In the example of FIGS. 8-9 the rear portion 808 comprises a rear wing portion 840 and a collar 842 (see FIG. 15). The rear wing portion 840 is attached to the rear edge 836 of the rim 816 of the base portion 806. The rear wing portion 840 covers a proximal exposed surface of the robot arm. Rear wing portion 840 is suitably shaped to match the shape of the proximal exposed surface of the robot arm. Suitably, the rear wing portion 840 is angled relative to a direction B perpendicular to the base portion 806 away from the distal end of the robot arm, by an angle α (see FIG. 15). For example, $20°<\alpha<50°$, or $30°<\alpha<40°$, or $35°<\alpha<37°$. Where the interface structure 802 is attached to the drape this aids the process of passing the drape over the robot arm.

The collar 842 is attached to the rear wing portion 840. Suitably, the collar 842 is integrally moulded with the rear wing portion 840. In the example of FIGS. 8-9, the collar has a substantially cylindrical inner surface. The collar 842 may have a substantially frustoconical outer surface The collar 842 may terminate in a sterile drape (not shown). Alternatively the locking element 804 (described in more detail blow) may terminate in a sterile drape (not shown). In either case the sterile drape shrouds the surgical robot arm. In practice, the interface assembly 700 is installed axially onto the robot arm, i.e. along the longitudinal axis of the drive assembly interface at the end of the robot arm. The drape is then unravelled down the robot arm.

The interface structure 802 may further comprise an envelope portion 810 that connects the longer of the outer edges 830, 832 of the base portion 806. These longer edges are those which run down the length of the base portion 806. As shown in FIGS. 8-9, the envelope portion 810 may circumscribe the drive assembly. The shape of the envelope portion 810 may match the shape of the outer surface of the robot arm at the drive assembly. Suitably, the envelope portion 810 contacts the exterior surface of the robot arm at the drive assembly. This contact may be a snug fit. This contact may be sheath-like. In this way, the envelope portion 810 bears on the exterior surface of the robot arm at the drive assembly. The envelope portion 810 thereby acts to retain the interface structure 802 to the robot arm. Specifically, the envelope portion 810 acts to retain the interface structure 802 to the robot arm in directions transverse to the longitudinal axis 824 of the interface structure 802.

Interface structure 802 may further comprise a front wing portion 812. Front wing portion 812 is attached to the front edge 828 of the rim 816 of the base portion 806. Suitably, the front wing portion 812 is integrally moulded with the base portion and envelope portion of the interface structure. The front wing portion 812 covers a distal exposed surface of the surgical robot arm. The inner surface of the front wing portion 812 may be shaped to match the shape of the distal exposed surface of the robot arm. The outer surface of the front wing portion 812 may be shaped to match the shaped of the front of the instrument.

The base portion 806 may support a plurality of second fasteners 848a, 848b, 848c, 848d for engaging the surgical instrument so as to retain the surgical instrument to the interface structure. These second fasteners 848a, 848b, 848c, 848d protrude from the first surface 814 of the base portion 806 transverse to the first surface 814. The second fasteners 848a, 848b, 848c, 848d protrude from the longer of the outer edges 830, 832 of the base portion 806. These longer edges are those which run down the length of the base portion 806. These longer edges are those which connect the first surface and the side flange portions. In the example of FIGS. 8-9, there are four second fasteners. There may, however, be more than four, or fewer than four, second fasteners. Preferably, there are at least two second fasteners, one on either longer outer edge 830, 832, in order to prevent the instrument from dislodging from the interface assembly in a direction perpendicular to the longitudinal axis 824 of the interface structure. In other words, to prevent the instrument from dislodging from the interface assembly in a direction perpendicular to the longitudinal axes 614 and 409 of the terminal link of the robot arm and the instrument shaft respectively, when the instrument is engaged with the robot arm.

The second fasteners 848*a*, 848*b*, 848*c*, 848*d* may be integrally formed with the base portion 806.

When the instrument is interfaced to the robot arm, via the interface assembly 700, the performance of the instrument is linked to the quality of the connection of the instrument, via the interface assembly 700, to the arm. One measure of the quality of the connection is the ability of the instrument interface, and thus the instrument, to be retained on the arm in the right place. Accordingly, the interface assembly 700 also comprises a locking element 804 to lock the interface structure 802 to the robot arm. By ensuring that the interface assembly 700, and thus the instrument, are retained on the arm in the right place during use the locking element 804 may improve performance of the instrument.

Figure 10:
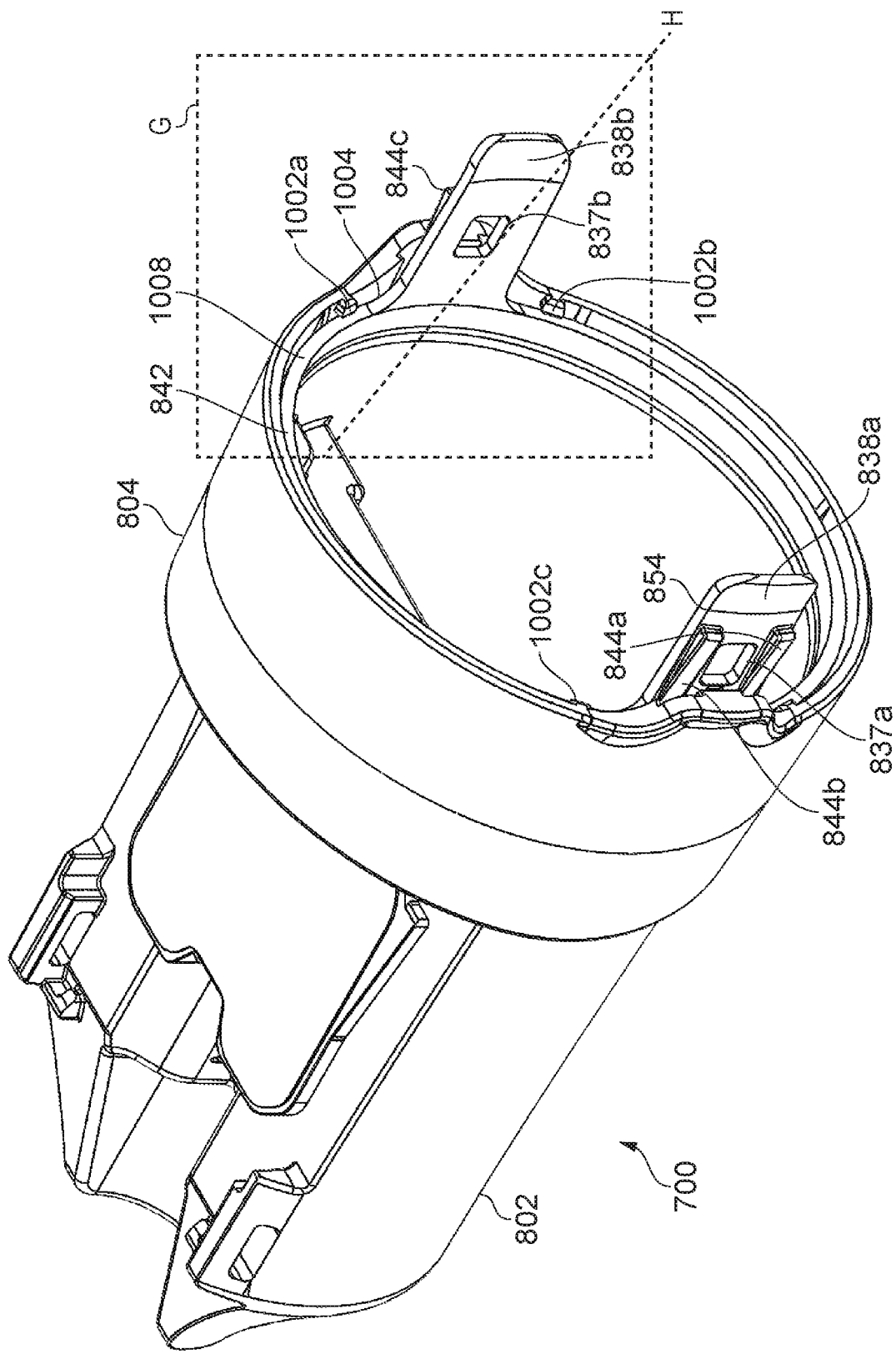
FIG. 10 illustrates a rear view of the interface assembly of FIG. 8 in isolation.

The locking element 804 is moveably mounted to the rear portion 808 of the interface structure. The locking element 804 is moveable between an unlocked position (FIG. 8) and a locked position (FIGS. 9-10). In the locked position the locking element 804 biases the first fasteners 838*a*, 838*b* inwards to lock the interface structure 802 onto the robot arm. That is, the locking element biases the first fasteners 838*a*, 838*b* towards the surgical robot arm when the interface assembly 700 is attached to the surgical robot arm. In contrast, in the unlocked position the locking element 804 does not bias the first fasteners 838*a*, 838*b* inward (e.g. towards the surgical robot arm when the interface assembly is attached to the surgical robot arm). As shown in FIGS. 8-9, the locking element 804 may be a cylindrical surface wherein the diameter of the cylinder is larger than the diameter of the collar 842 so that the locking element 804 can be mounted on the outside of the collar 842. The locking element 804 may be frustoconical. However, in other examples, the locking element 804 may take a different shape so long as the locking element is able to provide significant pressure on the first fasteners 848*a*, 848*b* to ensure the first fasteners 848*a*, 848*b* don't come dislodged from the robot arm (e.g. the lugs 839*a*, 839*b* described below) during use. For example, where the locking element is made of a stiff material, such as, but not limited to fibre reinforced plastic and magnesium (e.g. similar to the used in camera bodies), the locking element may alternatively have a semi-circle cross section. Where the locking element 804 is rotatable between the locked position and the unlocked position the locking element 804 may be generally cylindrical shaped with cut-outs for the first fasteners and when the locking element is in the unlocked position the cut-outs are aligned with the first fasteners so that the locking element does not engage the first fasteners.

In the example of FIGS. 8-9 the locking element 804 is slideable along the collar 842 in a direction parallel to the longitudinal axis of the interface structure to move between the unlocked position and the locked position. Specifically, the locking element is slideable in direction K to move from the unlocked position to the locked position and is slideable in direction L to move from the locked position to the unlocked position. In this example, as the locking element 804 slides into the locked position the locking element 804 engages the first fasteners 838*a*, 838*b* and pushes the first fasteners 838*a*, 838*b* inward. That is, the locking element 804 pushes the first fasteners towards the robot arm and onto the lugs 839*a*, 839*b* of the robot arm when the interface assembly is attached to the surgical robot arm. In other examples the locking element 804 may be rotatable about the collar 842 (e.g. in direction Z) to move between the unlocked position and the locked position.

The first fasteners 838*a*, 838*b* may comprise one or more sloped protrusions or ramps 844*a*, 844*b*, 844*c* on an outer surface 854 of the first fasteners 838*a*, 838*b* which aid the locking element 804 in biasing the first fasteners 838*a*, 838*b* inward (e.g. toward the robot arm). The sloped protrusions or ramps 844*a*, 844*b*, 844*c* are also shown in FIG. 10. Advantageously the depth of the sloped protrusions 844*a*, 844*b*, 844*c* increases in the direction in which the locking element 804 moves into the locking position so that as the locking element 804 moves into the locked position the pressure the locking element 804 applies to the first fasteners 838*a*, 838*b* increases. For example, in FIGS. 8-9 the locking element 804 is slideable in direction K (FIG. 8) to move from the unlocked position to the locked position thus the depth of the sloped protrusions increases in direction K. In contrast, where the locking element 804 is rotatable in direction Z, for example, to move from the unlocked position to the locked position the depth of the sloped protrusions may increase in direction Z.

In the example shown in FIGS. 8-9, each first fastener 838*a*, 838*b* comprises two sloped protrusions 844*a*, 844*b*, 844*c* (only three are shown), one on either side of the aperture 837*a*, 837*b* of the first fastener 838*a*, 838*b*. This allows the locking element 804 to apply substantially equal pressure across the first fasteners 838*a*, 838*b* when in the locked position to ensure the first fasteners 838*a*, 838*b* remain attached to the robot arm during use. In contrast, if the first fastener 838*a* of FIGS. 8-9 has only a single sloped protrusion 844*a*, for example, then the bottom of the first fastener 838*a* may be held tight to the robot arm, but the top of the first fastener 838*a* may not be held as tight allowing the top portion of the first fastener 838*a* to slip off the lug 839*a*. However, in other examples, there may be more than two, or fewer than two, sloped protrusions 844*a*, 844*b*, 844*c* per first fastener 838*a*, 838*b*. For example, instead of having a single aperture that engages a single lug, the first fasteners may comprise two apertures that engage two different lug portions. In these examples, each first fastener may comprise a single sloped protrusion situated between the two apertures.

In other examples, instead of the sloped protrusions being on an outer surface of the first protrusions the one or more sloped protrusions may be on an inner surface of the locking element. In these cases, the depth of the sloped protrusion may decrease in the direction in which the locking element 804 moves into the locking position so that as the locking element 804 moves into the locked position the pressure the locking element 804 applies to the first fasteners 838*a*, 838*b* increases.

When the surgical instrument is detached from the surgical robot arm, the interface assembly 700 is retained in the surgical robot arm. The interface assembly is more securely attached to the surgical robot arm than the instrument interface elements are to the drive assembly interface elements. Thus, the interface assembly 700 and the drape, remain attached to the surgical robot arm during instrument exchange. This is important in order to reduce the time taken to change instruments, since the interface structure does not need to be re-attached to the robot arm following detachment of an instrument. It is also important in order to reduce the likelihood of the drape tearing when changing instruments, which would cause the sterile operating environment to become contaminated with the non-sterile environment on the robot arm side of the drape. In the example of FIGS. 8-9, this is achieved by the shape of the envelope portion 810 surrounding the exterior of the robot arm at the drive assembly, and by the envelope portion 810 connecting to the base portion 806 wholly along the length of the sides 830 and 832. When a force is applied transverse to the base portion 806, away from the surgical robot arm, the envelope portion 810 is more resistant to breaking and hence dislodging from its retained position relative to the surgical robot arm than the instrument interface elements are from dislodging from their retained positions in the drive assembly interface elements.

The locking element 804 and/or the interface structure 802 may comprise one or more locking features to aid the locking element 804 in locking the interface structure 802 to the robot arm. Example locking features will be described with reference to FIGS. 10-14D.

Figure 11:
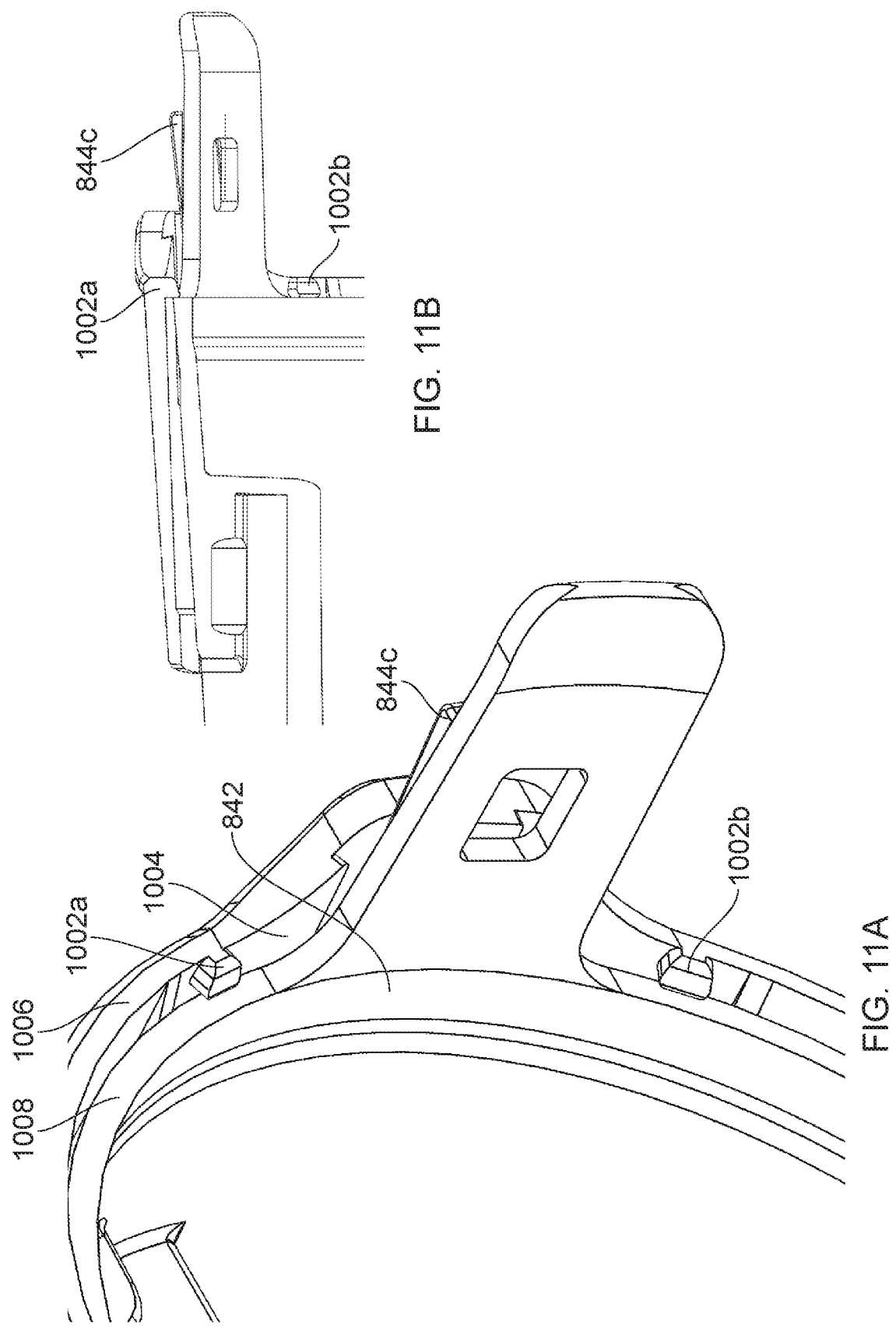
FIG. 11A illustrates a perspective view the first fasteners of FIG. 10.
FIG. 11B illustrates a side view of the first fasteners of FIG. 11B.
Figure 12:
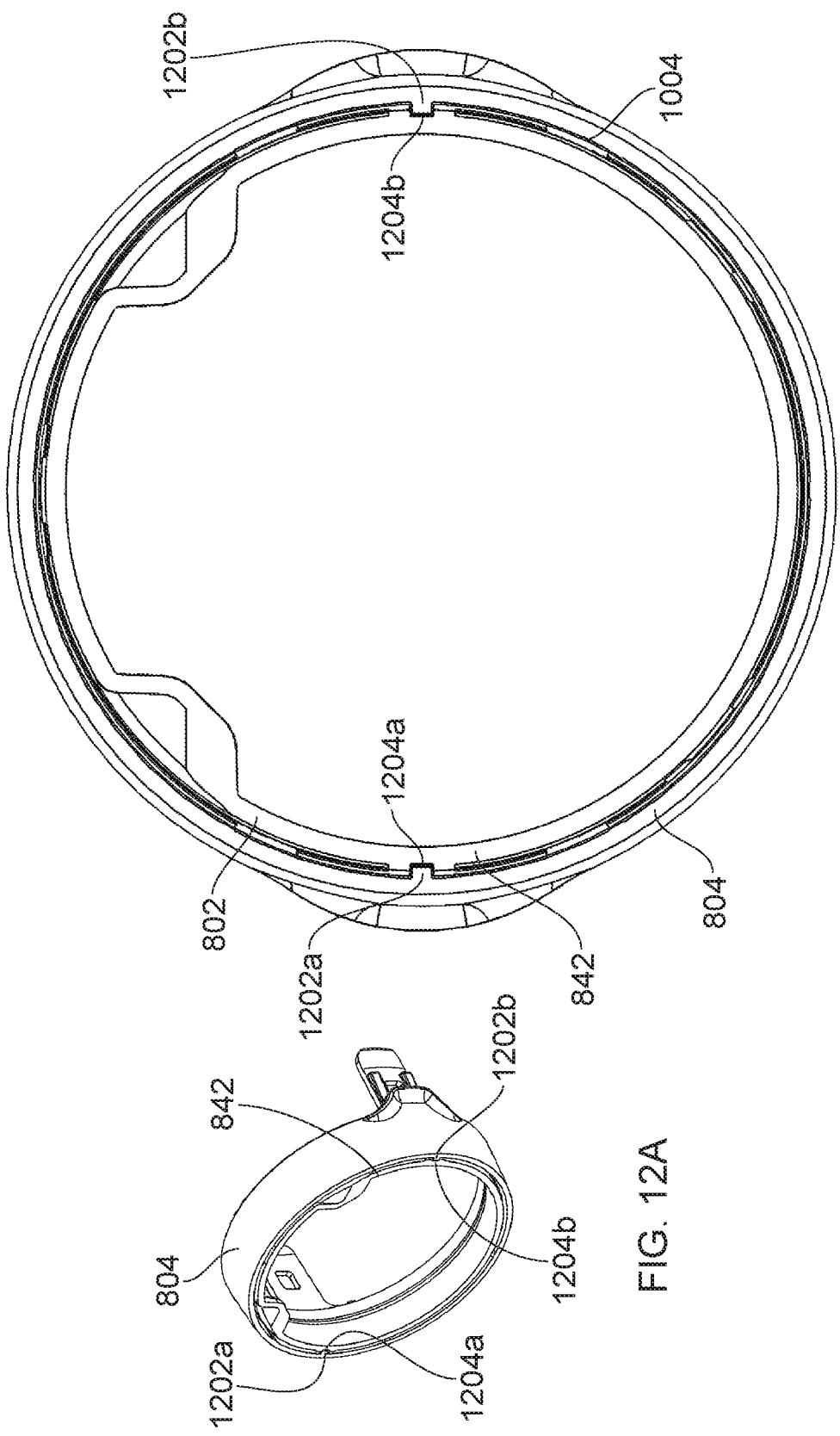
FIG. 12A illustrates a perspective view of a cross-section of the interface assembly of FIG. 8.
FIG. 12B illustrates a front view of the cross section of the FIG. 12A.

FIGS. 10, 11A and 11B show a rear view of all or portion of the locking assembly 700 of FIGS. 8-9. Specifically, FIG. 10 shows a rear view of the interface assembly 700 of FIGS. 8-9 in isolation where the locking element 804 is in the unlocked position, FIG. 11A shows an exploded view of area G of the locking assembly of FIG. 10, and FIG. 11B shows a cross-section of the locking assembly of FIG. 10 along line H-H. As shown in FIGS. 10-11B the locking element 804 may comprise one or more retention protrusions or tabs 1002a, 1002b, 1002c (FIGS. 10, 11A and 11B) that engage the rear portion 808 of the interface structure 802 when the locking element 804 is in the unlocked position so as to retain the locking element 804 on the interface structure 802 when the locking element 804 is in the unlocked position.

As shown in FIGS. 10-11B the retention protrusions 1002a, 1002b, 1002c may protrude from an inner surface 1004 of the locking element 804 proximate a distal edge 1006 of the locking element 804. When the locking element 804 is in an unlocked position the retention protrusions 1002a, 1002b, 1002c engage a rear edge 1008 of the collar 842 of the rear portion 808. The retention protrusions 1002a, 1002b, 1002c prevent the locking element from moving more than a predetermined distance from the locked position. In some cases, the retention protrusions 1002a, 1002b, 1002c may prevent the locking element 804 from moving more than about 12 mm from the locked position. In the example of FIGS. 10-11B there are four retention protrusions (only three are shown), one to engage the collar 842 on each side of the first fasteners 838a, 838b. However, in other examples there may be more or fewer than four retention protrusions 1002a, 1002b, 1002c.

In some cases, the locking element 804 may be removable from the interface structure 802. In these cases, the locking element 804 may be mounted on the interface structure 802 by sliding the locking element 804 over the front end of the interface structure 802 (e.g. over the front wing portion 812) in the direction K until the retention protrusions 1002a, 1002b, 1002c are situated on the rear side of the collar 842. To aid the retention protrusions 1002a, 1002b, 1002c in sliding over the collar 842 the collar 842 may comprise recessed portions 1510a, 1510b (FIG. 15) which align with the retention protrusions 1002a, 1002b, 1002c when the locking element engages the interface structure 802.

FIGS. 12A and 12B show a perspective view and a front view respectively of a cross-section of the interface assembly 700 of FIGS. 8-9 along line J-J. As shown in FIGS. 12A-12B the locking element 804 may comprise one or more ribs 1202a, 1202b which engage corresponding channels 1204a, 1204b of the rear portion 808 to prevent the locking element 804 from rotating with respect to the interface structure 802 when the locking element 804 is engaged with the interface structure 802. As shown in FIGS.

12A and 12B, the ribs 1202a, 1202b may be formed on an inner surface 1004 of the locking element 804 and extend radially (e.g. in a direction parallel to the longitudinal axis of the interface structure 802) across all or a portion of the locking element 804. Similarly, as shown in FIGS. 12A and 12B the corresponding channels 1204a, 1204b may be formed on an outer surface of the rear portion. Specifically, the channels 1204a, 1204b (also shown in FIG. 15) may extend across the collar 842 and across a portion of the first fasteners 838a, 838b. In the example of FIGS. 12A and 12B there are two channels 1204a, 1204b which are each aligned with a centre of a first fastener 838a, 838b. However, in other examples there may be more or fewer channels and/or the channels may be in a different position on the rear portion 808.

Figure 13:
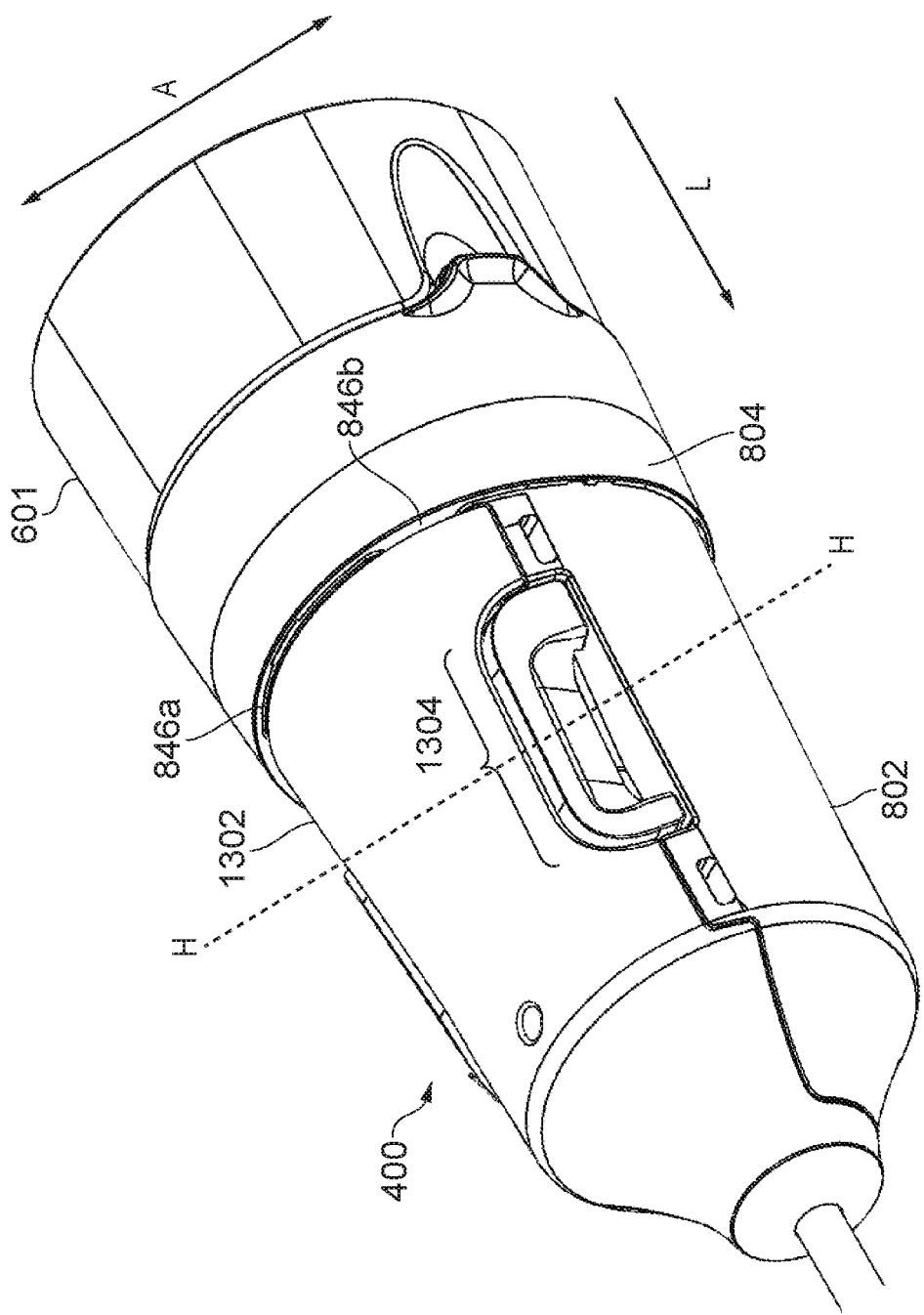
FIG. 13 illustrates an instrument attached to a robot arm via the interface structure of FIG. 9.

FIG. 13 illustrates an instrument attached to a robot arm via the interface assembly of FIGS. 8-9. As shown in FIGS. 8-9 the locking element 804 may comprise one or more instrument protrusions or tabs 846a, 846b that extend from a front edge 848 of the locking element 804 towards the front edge of the base portion 806. When an instrument is attached to a robot arm via the interface assembly 700 the instrument protrusions 846a, 846b are received in an opening or cut-out in the surgical instrument (FIG. 13). Then if the locking element 804 is accidentally moved out of the locked position the instrument protrusions or tabs 846a, 846b move into engagement with (e.g. bear against) the instrument to limit the movement of the locking element 804 from the locked position. In some cases, the instrument protrusions or tabs 846a, 846b may limit the locking element 804 from moving more than 1 mm from the locked position. In other words, the instrument protrusions or tabs 846a, 846b prevent the locking element 804 from moving a substantial amount from the locked position when an instrument is attached to the interface assembly. In the example shown in FIGS. 8-9 and 13 there are two instrument protrusions 846a, 846b. However, in other examples, there may be more or fewer instrument protrusions 846a, 846b.

Figure 14C:
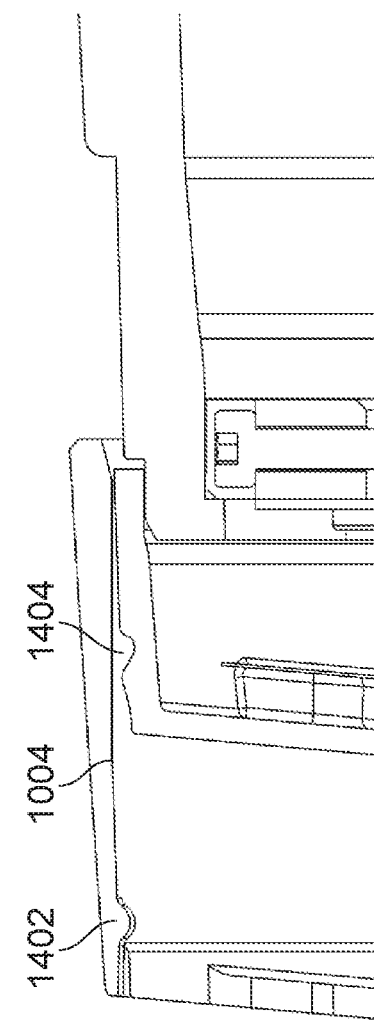
FIG. 14C illustrates a partial side view of the cross-section of FIG. 14A.
Figure 14D:
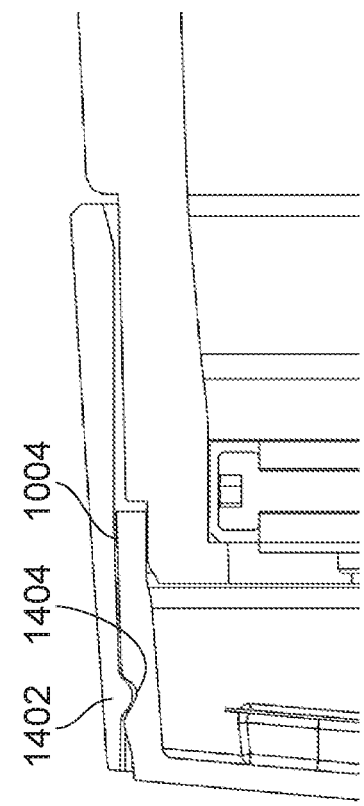
FIG. 14D illustrates a partial side view of the cross-section of FIG. 14B.
Figure 14A:
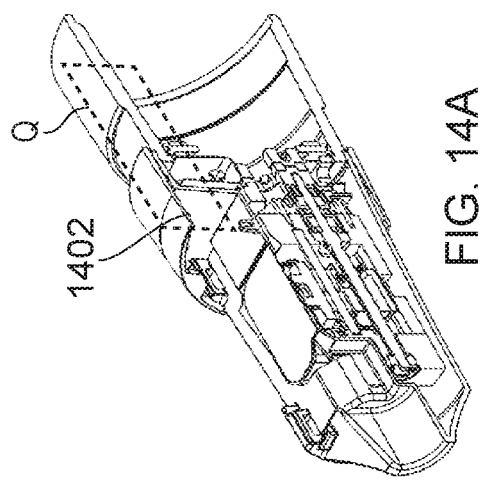
FIG. 14A illustrates a perspective view of a cross-section of the interface assembly of FIG. 8 attached to a robot arm when the locking element is in the unlocked position.
Figure 14B:
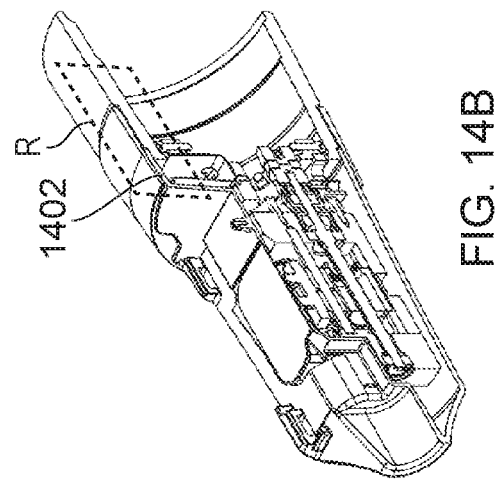
FIG. 14B illustrates a perspective view of a cross-section of the interface assembly of FIG. 8 attached to a robot arm when the locking element is in the locked position.

FIGS. 14A and 14B illustrate a perspective view of a cross-section of the interface assembly of FIGS. 8-9 along line X-X. FIG. 14A shows the locking element 804 in the unlocked position and FIG. 14B shows the locking element 804 in the locked position. FIGS. 14C and 14D show a side view of the areas Q and R of the interface assembly of FIGS. 14A and 14B respectively. As shown in FIGS. 14A-14D the locking element 804 may comprise one or more juts 1402 on an inner surface 1004 of the locking element 804 that engage with corresponding detent(s) or indentations 1404 on an outer surface of the rear portion 808 when the locking element 804 is in the locked position (FIGS. 14B, 14D). The engagement of the juts 1402 and the detents 1404 aid in retaining the locking element 804 in the locked position. In the example shown in FIGS. 14A-14D the juts 1402 are situated on an inner surface of the locking element proximate the front edge of the locking element 804 and the corresponding detents 1404 are situated on an outer surface of the collar 842 proximate a front edge of the collar so that the juts 1402 only engage the detents 1404 when the locking element is moved into the locked position. Where there is more than one jut and more than one detent 1404, the juts and the detents may be equally spaced around the locking element 804 and collar 842 respectively. Testing has shown that three equally spaced juts and detents are particularly effective in retaining the locking element in the locked position as in this configuration the locking element 804 applies an equal force around the circumference of the collar 842. In some examples, there may be a single jut that extends around the circumference of the inner surface 1004 of the locking element 804 that engages a single detent that extends around the circumference of the outer surface of the rear portion 808.

In some cases, the one or more juts 1402 and the corresponding detent(s) 1404 may be shaped so that when a jut 1402 engages the corresponding detent 1404 the user receives feedback that the locking element 804 has been successfully moved into the locked position. The feedback may be audible. For example, the user may hear an audible click, or the like, when the juts 1402 are brought into engagement with the detents 1404. Alternatively, or in addition, the feedback may be force feedback. For example, the user may feel a bump, or similar force feedback, when the user moves the locking element 804 into the locked position.

It will be evident to a person of skill in the art that the interface assembly 700 may have any combination of the features described with respect to FIGS. 10-14D.

As described above, in some cases, the proper alignment of the instrument interface 400 with the interface assembly may be maintained via a valley shaped opening 820 in the interface structure 802 and a pin 834. However, this configuration may be inadequate in some cases, particularly where the pin is formed on a thin section of plastic. Accordingly, in some cases the interface structure 802 may comprise one or more additional instrument alignment features to aid in aligning the instrument interface 400 with the interface assembly 700. The one or more instrument alignment feature may provide a tight, but not interference fit, between the instrument interface 400 and the interface assembly 700. Example instrument alignment features will be described with reference to FIGS. 15-17.

FIG. 15 illustrates the interface structure 802 of FIGS. 8-9 in isolation. To improve instrument-interface alignment the pin 834 on the base portion 806 may provide transverse alignment of the instrument only. To achieve this the pin 834 may have an oval shape which engages with a round recess 512 in the instrument interface. In some cases, the oval may be longer in a direction transverse to the longitudinal axis 824 of the interface structure 802 and is shorter in a direction parallel to the longitudinal axis 824 of the interface structure 802. Alternatively, the pin 834 may have a round shape and the corresponding recess 512 in the instrument interface 400 may have a rectangular shape.

To ensure a tight fit between the instrument interface 400 and the interface structure 802 in a direction transverse to the longitudinal axis of the interface structure 824 one or more of the valley walls 822a, 822b may comprise one or more ribs 1502 which engage the instrument interface 400 when the instrument interface is engaged with the interface structure 802. The ribs 1502 of FIG. 15 extend down towards the bottom of the valley. In the example of FIG. 15 there are two ribs 1502 (only one is shown), one on each valley wall 822a, 822b. However, in other example there may be more or fewer than two ribs 1502.

To improve the axial positioning of the instrument interface 400 with respect to the interface structure 802 the interface structure 802 may comprise one or more tabs 1504a, 1504b, 1506c, 1506d which bear against features of the instrument interface 400 in an axial direction (e.g. a direction parallel to the longitudinal axis of the instrument structure 802) when the instrument interface is brought into engagement with the interface structure 802. For example, as shown in FIG. 15 the interface structure 802 may have a first pair of tabs 1504a, 1504b that are situated on the front wing portion 812. The first pair of tabs 1504a, 1504b each have a surface 1508 facing the front of the interface structure 802 which engages a corresponding feature 514a, 514b (also shown in FIG. 5) of the instrument interface 400. The interface structure 802 may also, or alternatively, have a second pair of tabs 1506a, 1506b that are formed on the rim 816. The second pair of tabs 1506a, 1506b each have a surface 1510 facing the rear of the interface structure 8-2 which engages a corresponding feature 516a, 516b of the instrument interface 400. The second pair of tabs 1506a, 1506b may be formed as indentations in the rim 819 or may be separate from the rim 819.

Figure 16:
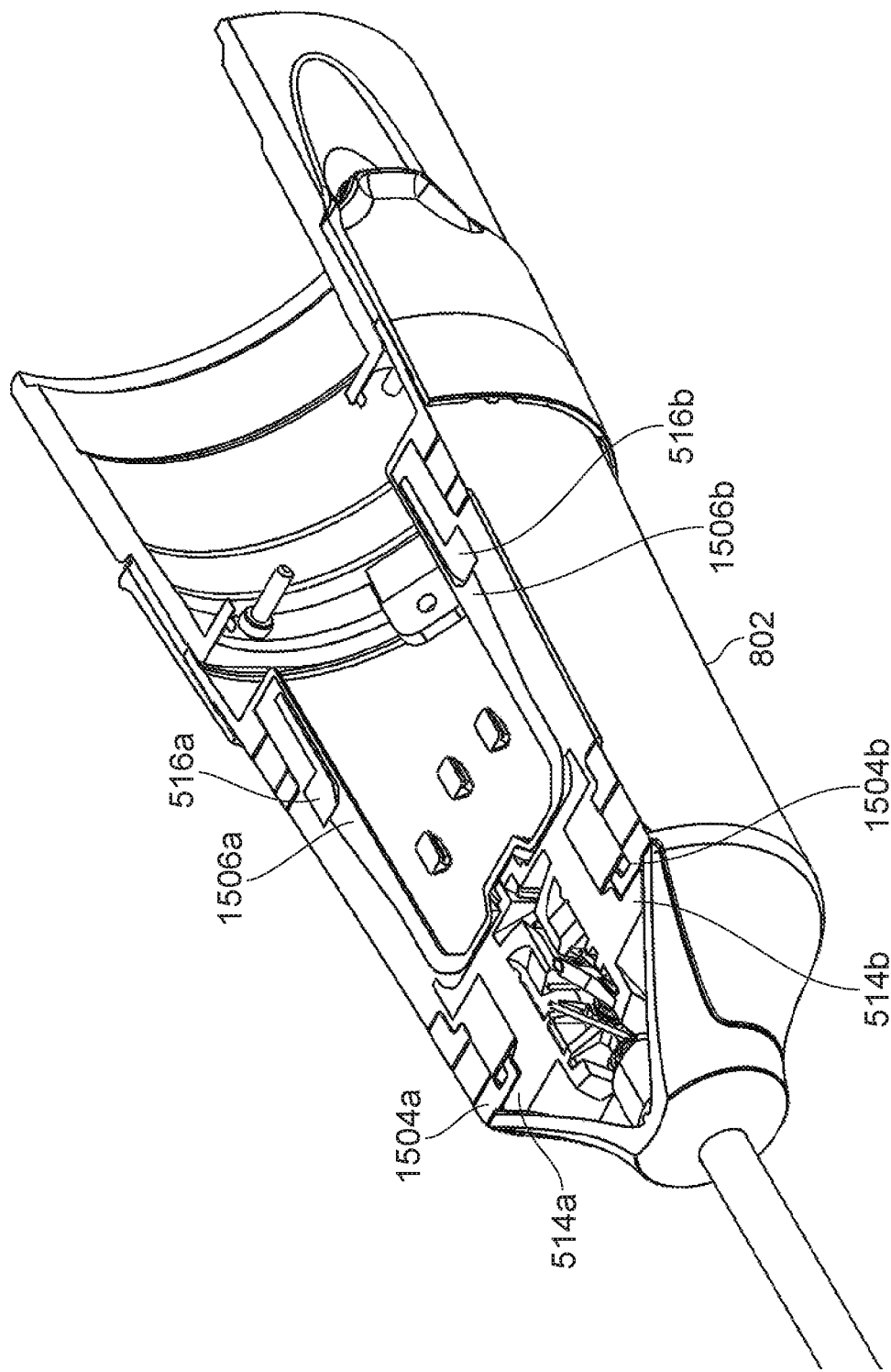
FIG. 16 illustrates a perspective view of a cross-section of an instrument interface attached to the interface assembly of FIG. 8.
Figure 17:
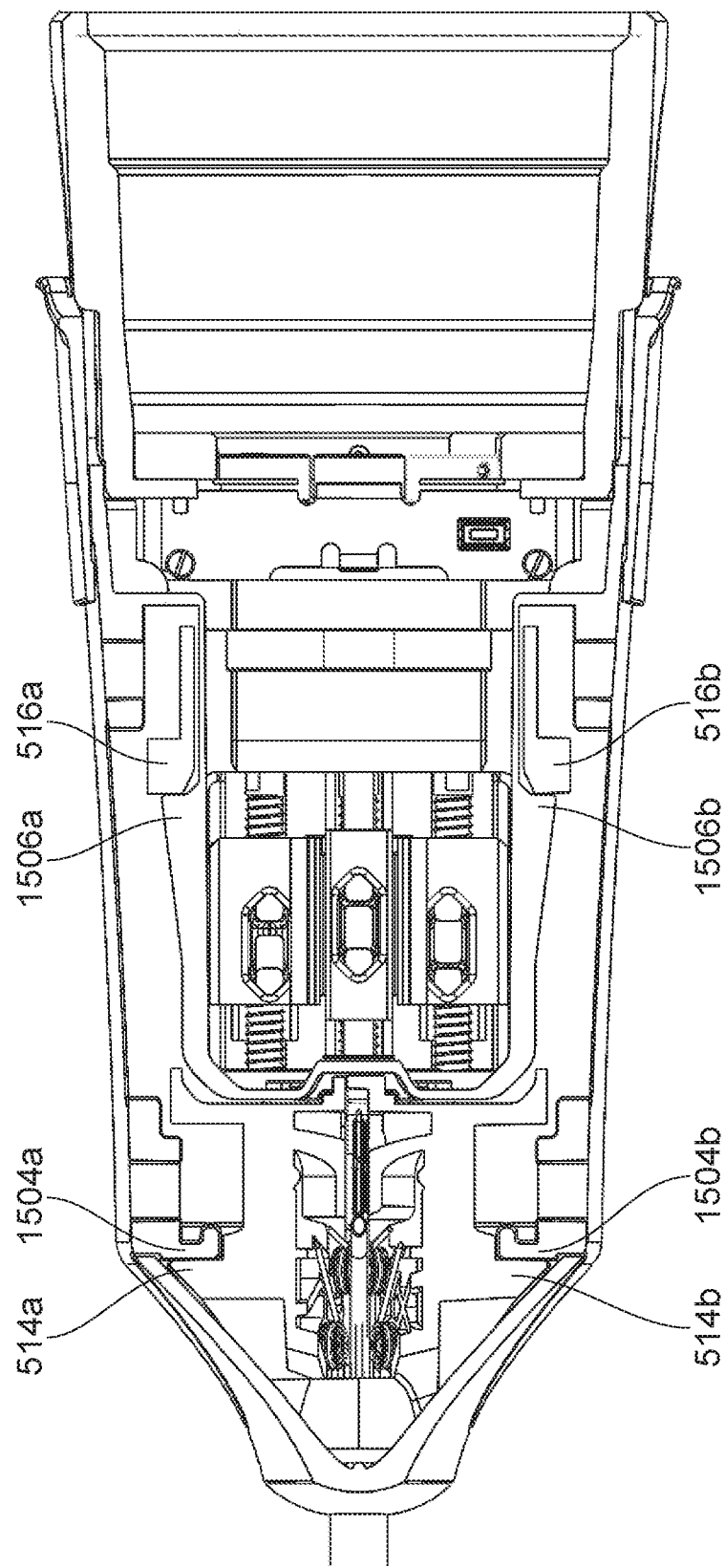
FIG. 17 illustrates a top view of the cross-section of FIG. 16.

FIGS. 16 and 17 illustrate a perspective view and a top view respectively of a partial cross-section of an instrument interface 400 engaged with an interface assembly 700 which shows the engagement of the instrument interface 400 and the first and second pairs of tabs 1504a, 1504b, 1506a, 1508b. Specifically, FIGS. 16 and 17 show the engagement of features 514a, 514b of the instrument interface 400 with the first pair of tabs 1504a, 1504b respectively when the instrument interface is engaged with the interface structure 802, and engagement of features 516a, 516b of the instrument interface 400 with the second pair of tabs 1506a 1506b respectively when the instrument interface is engaged with the interface structure. By adding tabs to the interface structure 802 that engage with existing features of the instrument interface 400 in the axial direction, the axial position of the instrument interface with respect to the interface structure 802 can be improved without having to modify the instrument interface 400.

As described above, when the instrument is interfaced to the robot arm, via the interface assembly 700, the performance of the instrument is linked to the quality of the connection of the instrument, via the interface assembly 700, to the arm. One measure of the quality of the connection is the ability of the instrument interface, and thus the instrument, to be retained on the arm in the right place. Accordingly, the performance of the instrument may be improved by the use of the locking element 804 to ensure that the interface assembly 700, and thus the instrument, are retained on the arm in the right place during use. Another measure of the quality of the connection is the stiffness of the connection. Typically, the stiffer the connection the more accurately movement of the robot is reflected in movement of the instrument. Accordingly, the performance of the instrument may further be improved by increasing the stiffness of the attachment of the interface assembly to the robot arm. To this end the interface structure 802 may comprise one or more stiffening features on its interior surfaces for interacting with the robot arm. Example stiffening features are described with reference to FIGS. 18A to 20.

Figure 18B:
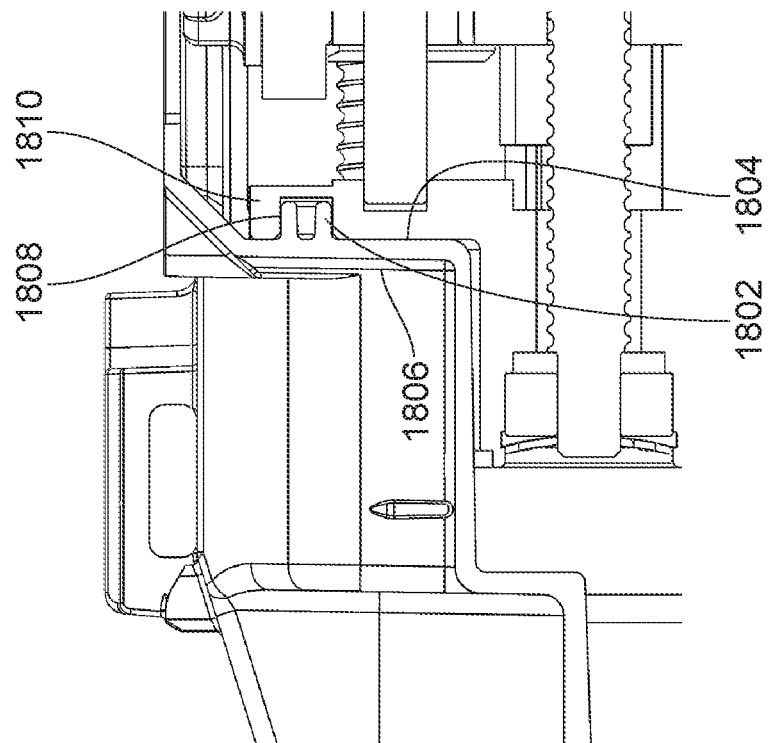
FIG. 18B illustrates a side view of a portion of the cross section of FIG. 18A.
Figure 18A:
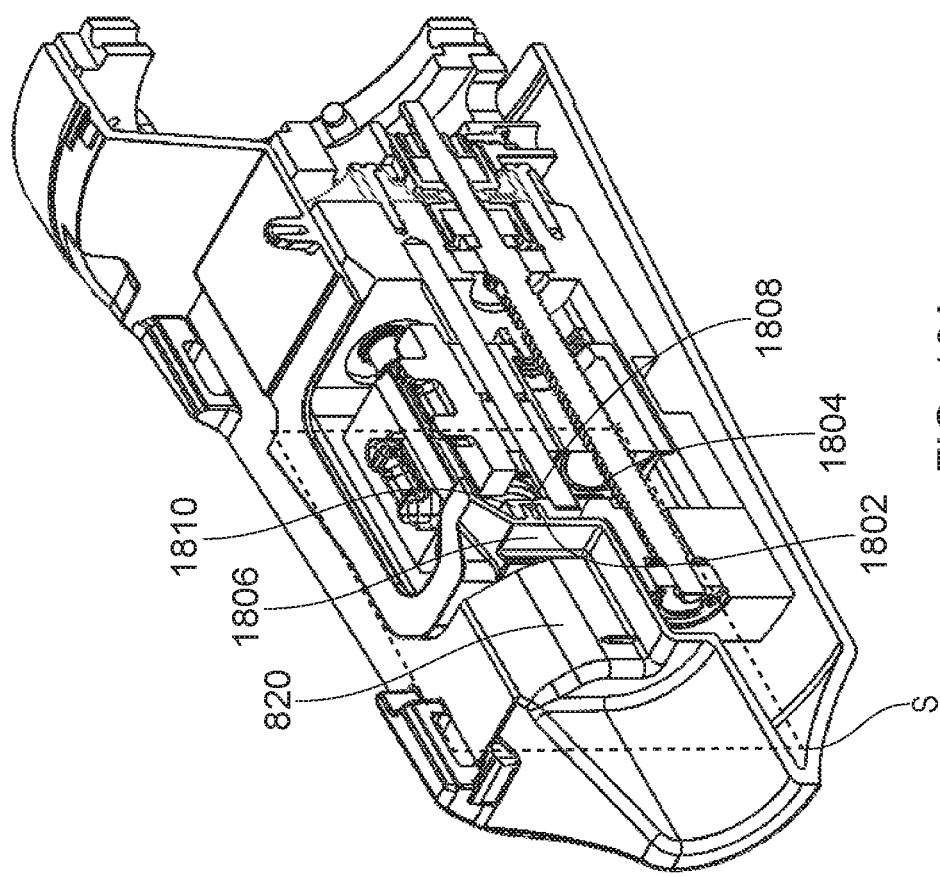
FIG. 18A illustrates a perspective view of a cross section of the instrument interface of FIG. 8 attached to a robot arm.

FIG. 18A illustrates a perspective view of a cross-section of the interface structure 802 of FIGS. 8-9 attached to a robot arm along X-X. FIG. 18B illustrates an exploded side view of the area S of FIG. 18A. As shown in FIGS. 18A and 18B an inner surface 1804 of the interface structure 802 may comprise a pin 1802 which is received in a recess 1808 in the robot arm when the interface structure 802 is brought into engagement with the robot arm. The recess 1808 is shaped such that when the pin engages the recess 1808 the interface structure 802 is restrained from moving in a direction perpendicular to the longitudinal axis 824 of the interface structure 802. In the example of FIGS. 18A and 18B the pin 1802 is situated on the inner surface 1804 of a rear wall 1806 of the opening 820. However, in other examples, the pin may be situated on another inner surface of the interface structure 802. The pin 1802 may be hollow.

Figure 19:
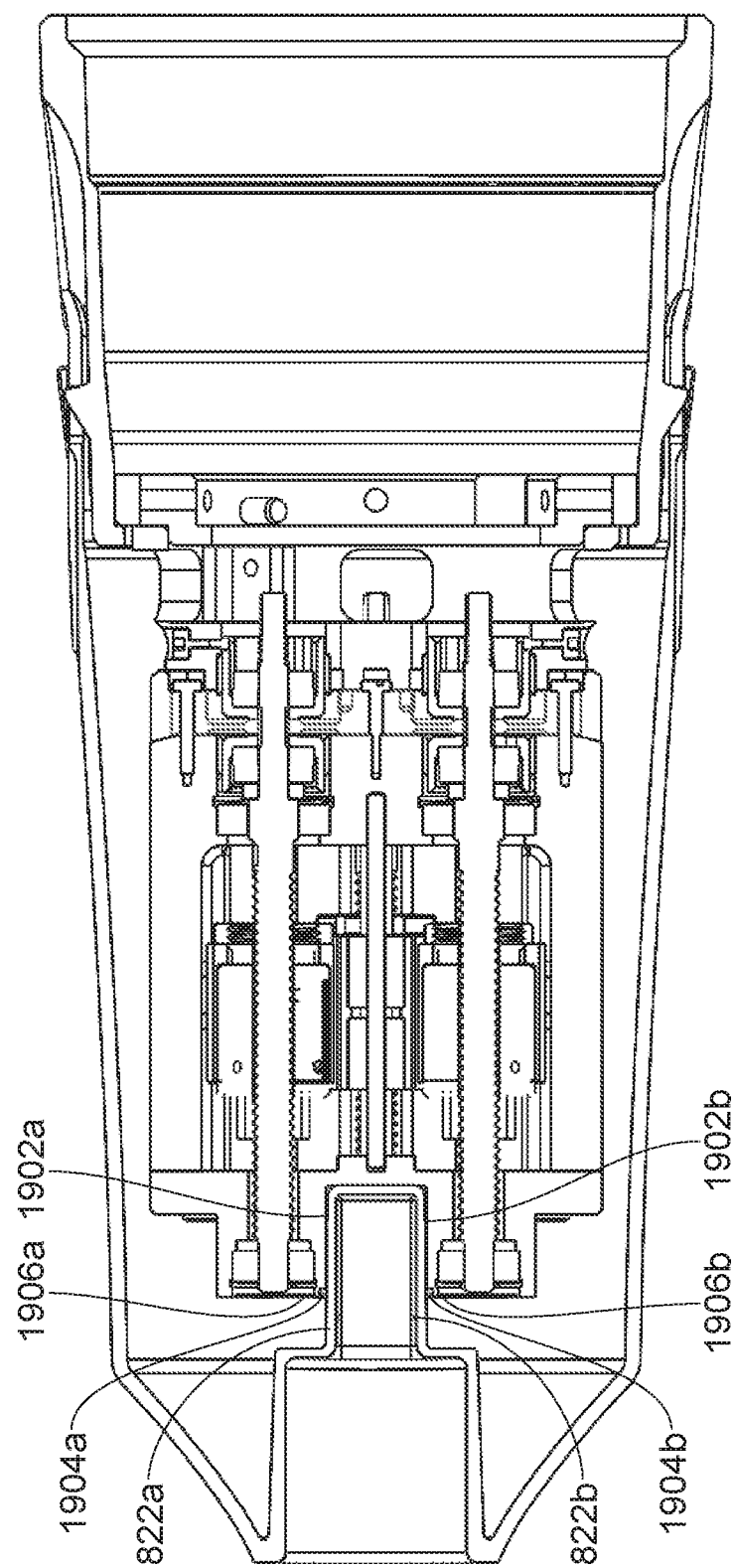
FIG. 19 illustrates a top view of a cross-section of the interface assembly of FIG. 8 attached to a robot arm.

FIG. 19 illustrates a top view of a cross-section of the interface structure 802 of FIGS. 8-9 attached to a robot arm along line Y-Y. As shown in FIG. 19 one or more inner surfaces 1902a, 1902b of the interface structure 802 may comprise a rib 1904a, 1904b which engage an outer surface 1906a, 1906b of the robot arm when the interface structure 802 is brought into engagement with the robot arm. The ribs act to resist motion of the interface structure 802 in the direction transverse to the longitudinal axis 824. In the example of FIG. 19, there is one rib 1904a, 1904b on an inner surface 1902a, 1902b of each valley wall 822a, 822b which create a tight fit with the corresponding valley walls at the distal end of the robot arm. However, in other examples the ribs may be situated on another inner surface of the interface structure 802.

Figure 20:
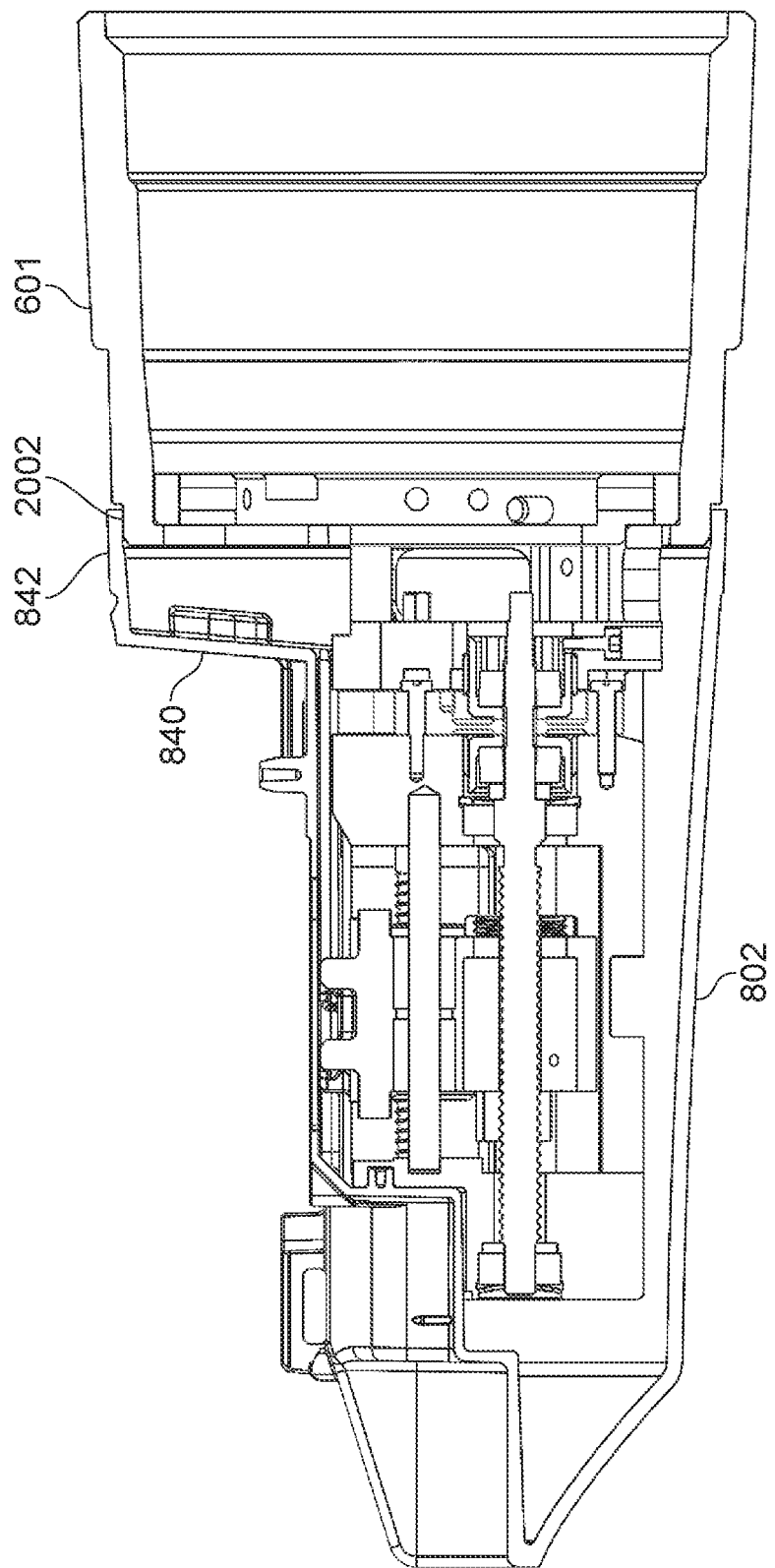
FIG. 20 illustrates a side view of a cross section of the interface assembly of FIG. 8 attached to a robot arm.

FIG. 20 illustrates a side view of a cross-section of the interface structure 802 of FIGS. 8-9 attached to a robot arm along line X-X. As shown in FIG. 20 the collar 842 of the rear portion 808 may be configured to have a light interference fit with a shoulder 2002 of the robot arm 601. In some cases, the shoulder 2002 may be configured to be concentric with a final roll joint axis of the robot arm. In these cases, having the collar 842 of the interface structure 802 have a light interface fit with the shoulder 2002 ensures that the collar 842 is concentric with the final roll axis as well enabling the instrument shaft to be aligned with the final roll axis.

FIG. 21A shows an instrument partially engaged with the interface assembly 700 of FIGS. 8-9 and FIG. 21B shows an instrument fully engaged with the interface structure 802 of FIGS. 8-9. As shown in FIGS. 21A and 21B the interface structure 802 may comprise one or more instrument engagement markings 2102a, 2102b that are visible when an instrument is not fully or properly engaged with the interface structure 802 (FIG. 21A), and that are not visible when an instrument is fully or properly engaged with the interface structure 802 (FIG. 21B). Such markings 2102a, 2102b provide a visual indication of whether the instrument has been properly engaged with the interface structure 802. The markings may have a distinct colour, such as, but not limited to, red, with respect to the remainder of the interface assembly 700. Having a distinct colour allows the instrument markings to stand out, making it easy for a person near to the robot arm to quickly determine whether the instrument is properly engaged with the interface assembly 700.

In the example of FIGS. 21A and 21B there are four instrument engagement markings 2102a, 2102b (only two are shown) divided into pairs. Each pair of engagement markings 2102a, 2102b is situated on the first surface 814 of the base portion 806 between a pair of second fasteners 848a, 848b, 848c, 848d such that when the instrument is completely or properly engaged with the interface structure 802 the pair of instrument engagement markings 2102a are covered by the engagement portion 1304 of the instrument. Specifically, in the example of FIGS. 21A and 21B each pair of instrument engagement markings 2102a, 2102b are covered up by opposite end portions 1306 of the engagement portion 1304. However, in other examples there may be more than four instrument engagement markings, or fewer than four instrument engagement markings, and/or the instrument engagement marking may be situated in another location so as to be covered by another component of the instrument.

As described above, FIG. 13 illustrates an engaged configuration of a surgical robot arm and a surgical instrument. In the example of FIG. 13, the surgical instrument comprises a body 1302 and two engagement portions 1304 (one shown), all of which cover the instrument interface 400 shown in FIGS. 4 and 5. The engagement portions are on opposing sides of the instrument interface. One engagement portion engages the second fasteners on one side of the instrument interface, and the other engagement portion engages the second fasteners on the other side of the instrument interface. Each engagement portion is displaceable relative to the body in direction A which is transverse to the longitudinal axis 409 of the instrument shaft 402. Each engagement portion 1304 is displaceable along the direction A towards the interior of the instrument.

The exterior body of the instrument 1302 and the exterior body of the robot arm is shaped to be frustoconical when the instrument is docked to the robot arm.

The engagement portion 1304 is biased towards adopting the engaged position. The engagement portion may, for example, be spring-loaded so as to bias its position towards the engaged position.

The interface structure 802 may further include a wireless receiver for receiving wireless transmissions from the surgical instrument. Preferably, the wireless receiver operates according to a communications protocol which has a short range, for example NFC, WiFi or Bluetooth. The receiver receives transmissions relating to the surgical instrument. For example, the receiver may receive transmissions relating to one or more of the following attributes of the surgical instrument: identity, type, origin, status, number of times used, length of time used, number of times left to use before expiry, length of time left to use before expiry. The wireless receiver may be located anywhere on the interface structure. Preferably, it is located on the side of the interface structure which faces the surgical robot arm. The wireless receiver may be a wireless transceiver which also incorporates a transmitter for transmitting wireless transmissions to the surgical instrument.

The surgical instrument may comprise a wireless transmitter for sending wireless transmissions to the interface structure as described above. The surgical instrument may comprise a wireless transceiver for sending and receiving wireless communications as described above.

Suitably, the interface assembly 700 is fastened to the drive assembly as the robot arm is being shrouded in the sterile drape as part of the set-up procedure prior to the operation beginning. Specifically, the interface assembly 700 (with the locking ring 804 mounted on the interface assembly 700 in the unlocked position) is push fitted onto the robot arm by applying force in the axial direction K (see FIGS. 8-9). This causes the first fasteners 838a, 838b to engage the robot arm. The locking element 804 is then pushed into the locked position so as to lock the interface assembly 700 to the robot arm. Once the interface assembly 700 has been locked onto the arm, the drape is unravelled down the robot arm.

At some point during the operation, the instrument may be exchanged for another instrument. The instrument is detached from the interface structure 802 by the user moving the engagement portion 1304 in the direction A until reaching the disengaged position. The user then lifts the instrument off the interface structure in a direction B which is perpendicular to the longitudinal axis 409 of the instrument shaft away from the interface structure. A different instrument can then be attached to the interface structure as previously described.

This method enables the instruments to be quickly and easily detached and attached to the robot arm during an operation without exposing the patient to a non-sterile environment. Since the instrument is removed by lifting it off the robot arm in a direction perpendicular to the shaft 402 of the instrument. Thus, there is no risk of pushing the instrument into the patient when detaching or attaching it.

The first fasteners depicted in the figures have the form of a clip for clipping into the recesses of the robot arm. The second fasteners depicted in the figures have the form of a socket for receiving a plug/nib from the instrument. However, the fasteners may take any suitable form, for example clips, clasps, buckles, latches, plugs, sockets, hooks, eyes, poppers, eyelets, buttons, Velcro, as long as the following criteria are satisfied:
1) the interface structure remains attached to the robot arm when the instrument is detached.
2) the interface structure, instrument and robot arm do not shift relative to each other as articulation of the instrument is driven by the robot arm so that the instrument will move and be actuated as expected in response to control signals generated by the console.

The instrument could be used for non-surgical purposes. For example, it could be used in a cosmetic procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. An interface assembly for detachably interfacing a surgical robotic arm to a surgical instrument, the interface assembly comprising:
an interface structure comprising:
a base portion comprising a first surface for facing the surgical instrument and a second surface for facing the surgical robotic arm; and
a rear portion attached to a rear edge of the base portion, the rear portion comprising one or more fasteners for engaging a proximal exposed surface of the surgical robotic arm so as to fasten the interface structure to the surgical robotic arm; and
a locking element moveably mounted on the rear portion, the locking element moveable relative to the rear portion between a locked position and an unlocked position, wherein when the locking element is in the locked position the locking element engages with the one or more fasteners to bias the one or more fasteners towards an engaged position and when the locking element is in the unlocked position the locking element does not engage with the one or more fasteners to bias the one or more fasteners towards the engaged position, wherein the locking element terminates in a drape and is attached to the drape.

2. The interface assembly of claim 1, wherein the locking element is slideable between the locked position and the unlocked position.

3. The interface assembly of claim 1, wherein the locking element has a cylindrical inner surface.

4. The interface assembly of claim 3, wherein the rear portion comprises a collar with a cylindrical inner surface and the locking element is moveable along the collar.

5. The interface assembly of claim 4, wherein the collar is configured to have an interference fit around a shoulder of the surgical robotic arm when the interface assembly is brought into engagement with the surgical robotic arm.

6. The interface assembly of claim 1, wherein an outer surface of one or more of the fasteners comprises one or more sloped protrusions.

7. The interface assembly of claim 1, wherein the locking element comprises one or more juts and each jut is configured to engage a detent in the rear portion when the locking element is in the locked position.

8. The interface assembly of claim 7, wherein the one or more juts and the detents are configured to generate feedback when the one or more juts come into engagement with the detents.

9. The interface assembly of claim 1, wherein a front surface of the locking element comprises one or more tabs configured to be received in an opening in the surgical instrument when the surgical instrument is brought into engagement with the interface assembly so as to restrict movement of the locking element from the locked position when the surgical instrument is engaged with the interface assembly.

10. The interface assembly of claim 1, wherein an inner surface of the locking element comprises one or more retention protrusions that engage a rear surface of the rear portion when the locking element is in the unlocked position so as to retain the locking element on the interface structure when the locking element is in the unlocked position.

11. The interface assembly of claim 1, wherein an inner surface of the locking element comprises one or more ribs that engage channels in an outer surface of the rear portion so as to prevent the locking element from rotating with respect to the interface structure.

12. The interface assembly of claim 1, wherein the interface structure further comprises an envelope portion which connects opposing edges of the base portion so as to, when engaged on the surgical robotic arm, retain the interface structure to the surgical robotic arm.

13. The interface assembly of claim 12, wherein the envelope portion is shaped so as to, when the interface structure is engaged on the surgical robotic arm, circumscribe an exterior surface of the surgical robotic arm.

14. The interface assembly of claim 1, wherein the base portion comprises an oval pin that is received in a circular recess in the surgical instrument when the surgical instrument is in engagement with the interface assembly, the oval pin being longest in a direction transverse to a longitudinal axis of the interface structure.

15. The interface assembly of claim 1, wherein the base portion comprises a round pin that is received in a slot-shaped recess in the surgical instrument when the surgical instrument is in engagement with the interface assembly.

16. The interface assembly of claim 1, wherein the interface structure comprises one or more tabs that bear against features of the surgical instrument in a direction parallel to a longitudinal axis of the interface assembly when the surgical instrument is in engagement with the interface assembly so as to axially align the surgical instrument with the interface assembly.

17. The interface assembly of claim 1, wherein an inner surface of the interface structure comprises a pin that engages a corresponding slot-shaped recess in an outer surface of the surgical robotic arm when the interface assembly is engaged with the surgical robotic arm so as to restrain the interface structure from moving in a direction perpendicular to a longitudinal axis of the interface structure.

18. The interface assembly of claim 1, wherein the base portion comprises one or more instrument engagement markings that are visible when a surgical instrument is not fully attached to the interface assembly and that are not visible when a surgical instrument is fully attached to the interface assembly.

19. A surgical robotic arm for use in robotic surgery, the surgical robotic arm comprising:
   a base; and
   a series of articulations connecting the base to an interfacing portion at a distal end of the surgical robotic arm, the series of articulations enabling the interfacing portion to be articulated relative to the base; and
   the interfacing portion configured to interface a surgical instrument by retaining an interface assembly comprising:
      an interface structure comprising:
         a base portion comprising a first surface for facing the surgical instrument and a second surface for facing the surgical robotic arm; and
         a rear portion attached to a rear edge of the base portion, the rear portion comprising one or more fasteners for engaging a proximal exposed surface of the surgical robotic arm so as to fasten the interface structure to the surgical robotic arm; and
         a locking element moveably mounted on the rear portion, the locking element moveable relative to the rear portion between a locked position and an unlocked position, wherein when the locking element is in the locked position the locking element engages with the one or more fasteners to bias the one or more fasteners towards an engaged position and when the locking element is in the unlocked position the locking element does not engage with the one or more fasteners to bias the one or more fasteners towards the engaged position, wherein the locking element terminates in a drape and is attached to the drape.

* * * * *